(12) United States Patent
Martin et al.

(10) Patent No.: US 7,320,679 B2
(45) Date of Patent: Jan. 22, 2008

(54) THERAPEUTIC USE OF GROWTH FACTOR, AND DELIVERY DEVICE, ESPECIALLY FOR THE TREATMENT OF INTIMAL HYPERPLASIA

(75) Inventors: John Francis Martin, London (GB); Seppo Yla-Herttuala, Kuopio (FI); Stephen George Edward Barker, London (GB)

(73) Assignee: Ark Therapeutics, Ltd. (GB)

( * ) Notice: Subject to any disclaimer, the term of this patent is extended or adjusted under 35 U.S.C. 154(b) by 500 days.

(21) Appl. No.: 10/370,291

(22) Filed: Feb. 19, 2003

(65) Prior Publication Data

US 2003/0225020 A1  Dec. 4, 2003

Related U.S. Application Data

(63) Continuation of application No. 09/297,486, filed as application No. PCT/GB97/03015 on Nov. 3, 1997.

(30) Foreign Application Priority Data

| Nov. 1, 1996 | (GB) | ................... | 9622852.3 |
| May 9, 1997 | (GB) | ................... | 9709494.0 |
| Aug. 21, 1997 | (GB) | ................... | 9717791.9 |

(51) Int. Cl.
   *A61M 31/00* (2006.01)
   *A61M 5/00* (2006.01)

(52) U.S. Cl. ............... 604/93.01; 604/95.03; 604/264

(58) Field of Classification Search ............ None
   See application file for complete search history.

(56) References Cited

U.S. PATENT DOCUMENTS

| 3,797,485 | A | * | 3/1974 | Urquhart | ............... | 604/288.04 |
| 5,201,728 | A | * | 4/1993 | Giampapa | ............... | 604/891.1 |
| 5,326,568 | A | * | 7/1994 | Giampapa | ............... | 424/426 |
| 5,830,879 | A | * | 11/1998 | Isner | ............... | 514/44 |

FOREIGN PATENT DOCUMENTS

| WO | WO94/23668 | 10/1994 |
| WO | WO94/28721 | 12/1994 |
| WO | WO96/33673 | 10/1996 |

OTHER PUBLICATIONS

Joukov et al (J. Biol. Chem 273(12): 6599-6602, Mar. 1998).*
Olofsson et al (Proc. Nat. Acad. Sci. USA 93: 2576-2581, Mar. 1996).*
Laitinen et al (Circulation, (Oct. 15, 1996) vol.94, No. 8, Supp. S, pp. 3720).*
Zhang et al (J. Nat. Cancer Inst. 87(3): 213-219, 1995).*
Mitola et al (Blood, (Aug. 15, 1997) vol. 90, No. 4, pp. 1365-1372.*
Asahara, T. et al., "Local Delivery of Vascular Endothelial Growth Factor Accelerates Reendothelialization and Attenuates Intimal Hyperplasia in Balloon-Injured Rat Carotid Artery," *Circulation* 1995, vol. 91, No. 11, pp. 2793-2801.
Booth, R.F.G. et al., "Rapid Development of Atherosclerotic Lesions in the Rabbit Carotid Artery Induced by Perivascular Manipulation," *Atherosclerosis* 1989, vol. 76, No. 2,3, pp. 257-268.
Forte, P. et al., "Basal Nitric Oxide Synthesis in Essential Hypertension," *The Lancet* 1997, vol. 349, pp. 837-842.
Houck, K.A. et al., "The Vascular Endothelial Growth Factor Family: Identification of a Fourth Molecular Species and Characterization of Alternative Splicing of RNA," *Molecular Endocrinology* 1991, vol. 5, No. 12, pp. 1806-1814.
Laitinen, M. et al., "VEGF Gene Transfer Reduces Intimal Thickening Via Increased Production of Nitric Oxide in Carotid Arteries," *Human Gene Therapy* 1997, vol. 8, No. 15, pp. 1737-1744.
Laitinen, M. et al., "Local Adventitial VEGF Gene Transfer Reduces Neointima Formation in Rabbit Carotid Arteries," *Circulation* 1996, vol. 94, No. 8, p. 3720.
Morbidelli, L. et al., "Nitric Oxide Mediates Mitogenic Effect on VEGF on Coronary Venular Endothelium," *American Journal of Physiology* 1996, vol. 270, No. 1, pp. H411-H415.
Von Der Leyen, H.E. et al., "Gene Therapy Inhibiting Neointimal Lesion: In Vivo Transfer of Endothelial Cell Nitric Oxide Synthase Gene," *Proceedings of the National Academy of Sciences of USA*, 1995, vol. 92, pp. 1137-1141.
Zachary, I. et al., "Vascular Endothelial Growth Factor Stimulates Nitric Oxide Production and Prostacyclin Synthesis in Human Umbilical Vein Endothelial Cells," *European Heart Journal* 1997, vol. 18, abstract. No. 148.
European Search Report for Application No. EP 04 02 1613, Dec. 22, 2004.

* cited by examiner

*Primary Examiner*—Richard Schnizer
(74) *Attorney, Agent, or Firm*—Saliwanchik, Lloyd & Saliwanchik

(57) ABSTRACT

The present invention concerns vascular endothelial growth factor (VEGF) which has utility in the treatment of intimal hyperplasia, hypertension and atherosclerosis, and of conditions susceptible to treatment with agents that produce nitric oxide or prostacyclin. Instead of VEGF, an equivalent agent such as an agonist of VEGF receptors may be given, as may nucleic acid encoding such an agonist. The agent may successfully be administered via the adventitial surface of a blood vessel, e.g., using a device which defines a reservoir between the body wall and the vessel's adventitial surface, the reservoir being at least part-filled by a pharmaceutical formulation containing the agent to be delivered.

29 Claims, 3 Drawing Sheets

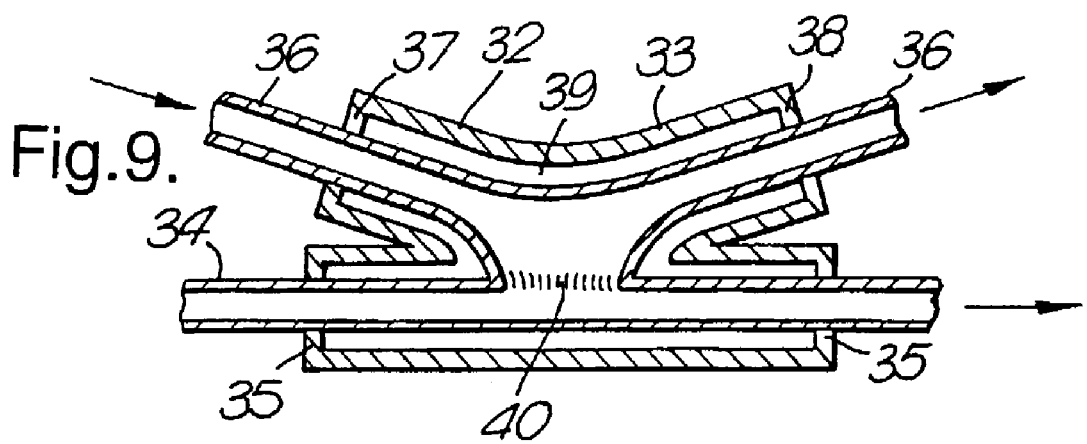
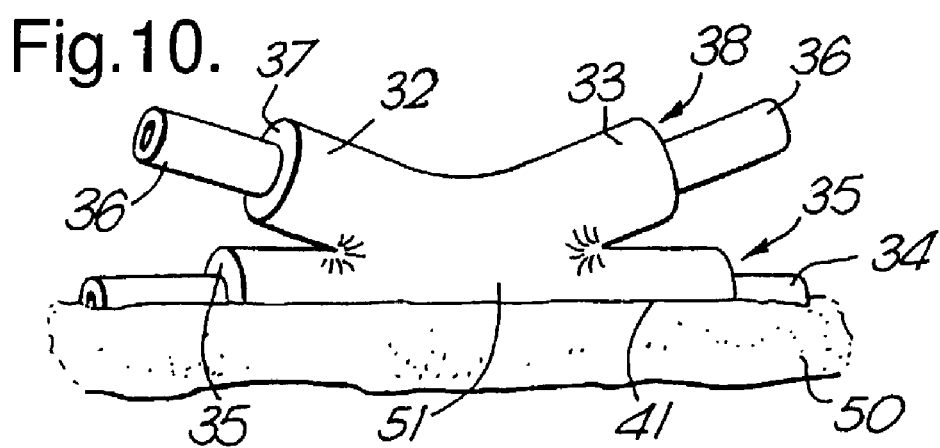
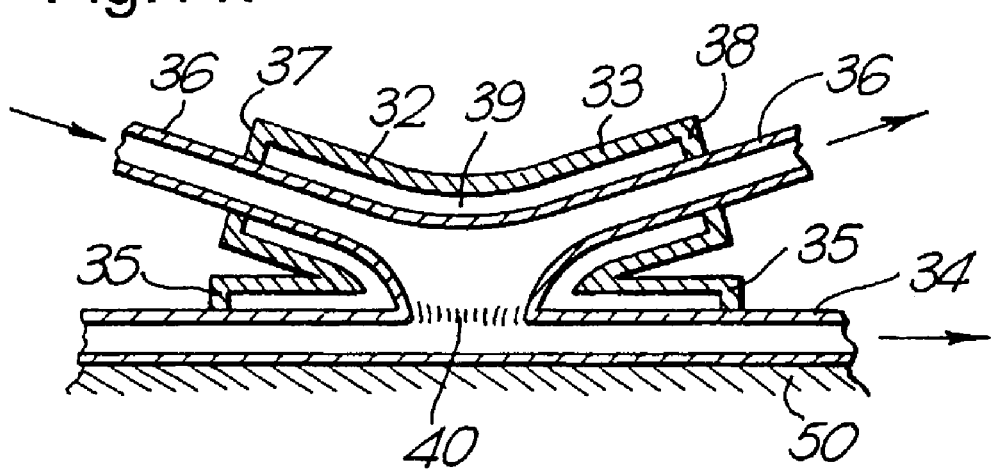

THERAPEUTIC USE OF GROWTH FACTOR, AND DELIVERY DEVICE, ESPECIALLY FOR THE TREATMENT OF INTIMAL HYPERPLASIA

CROSS-REFERENCE TO RELATED APPLICATION

This application is a continuation of U.S. application Ser. No. 09/297,486, filed Jun. 14, 1999, which is the U.S. national stage of international application No. PCT/GB97/03015, filed Nov. 3, 1997.

FIELD OF THE INVENTION

The present invention relates to the therapeutic use of a growth factor, and particularly to the treatment and prevention of intimal hyperplasia of blood vessels and other conditions, especially hypertension. The invention relates also to a device that can be used for delivering the active agent.

BACKGROUND OF THE INVENTION

Intimal hyperplasia is the increase in the number of cells between the endothelium and internal elastic lamina of a blood vessel, particularly in the intimal layer found there, or in an artery. Intimal hyperplasia is often caused by smooth muscle cell (SMC) proliferation in the blood vessel wall.

When intimal hyperplasia occurs, de novo thickening of the intimal layer or of the vessel wall, i.e. stenosis, may result. Thus, the blood vessel may become occluded.

Also, when an obstruction in a blood vessel has been cleared, intimal hyperplasia occurring after surgery may lead to the artery's becoming occluded again. This is known as restenosis.

Proliferation of arterial smooth muscle cells commonly occurs when a blood vessel, e.g. an artery, is deformed or disturbed during surgery. For example, intimal hyperplasia can lead to de novo stenosis following bypass grafts in which a vein is anastomosed to an artery, and following surgical anastomosis in general. Two examples of surgical procedures which can give rise to stenosis are coronary bypass grafts and above-knee femoro-popliteal arterial bypass grafts.

Similarly, restenosis can occur following balloon angioplasty procedures used to clear obstructions in blood vessels, for example balloon angioplasty procedures.

Intimal hyperplasia, whether it leads to stenosis or restenosis, remains a major problem after various surgical procedures.

Atherosclerotic cardiovascular disease is the leading cause of death in Europe and North America and prompts a highly significant morbidity consequent upon occlusion of the arterial lumen, either preventing or reducing blood flow, thrombosis superimposed upon a plaque, with possible distal embolisation, arterial wall weakening, leading to aneurysmal dilation and eventual rupture. Dependant upon site and disease distribution, several options for treatment exist, with arterial bypass grafting the most common surgical intervention. For coronary artery disease, this has now become the most common surgical procedure of all in the United States with >200,000 operations performed each year since 1990 and with >20,000 operations performed each year in the United Kingdom. In the aorta, renal, mesenteric and peripheral vessels, the burden of surgical bypass procedures continues to increase, with operation rates in the United States and Europe of 35-70 per 100,000 population. In combination, the number of surgical bypass procedures performed each year approximates one million.

In the first 24 months following surgery, a very significant number of arterial bypass grafts fail (occlude). Quoted values range from 20% to 30%. This means that for all cardiac and peripheral arterial bypass procedures performed each year in the United Kingdom (approximately 25,000-30,000), between 6,000 and 7,000 may be expected to fail, within two years. Failure rates for 're-do' procedures are even higher. Such is the financial cost of failure that, in the United States, it has been calculated that even a modest decrease in failure rates following coronary procedures, from 33% to 25%, might save up to $750 million from the healthcare budget.

There are three main causes for graft failure within five years from surgery. The first is recognised to occur early, within 30 days of the operation (<5%), and represents technical error (e.g. poor anastomotic technique). Later failure, after 24 months, is generally as a result of progression of the original atherosclerotic process. However, it is those grafts that occlude between one and 24 months that form the majority of failures (<70%). In these cases, it is SMC intimal hyperplasia that is responsible for progressive narrowing, i.e. stenosis, of the arterial lumen, resulting eventually in complete occlusion. Typically, the SMC intimal hyperplasia is sited around the distal arterial anastomosis and the native vessel wall opposite the anastomosis. It is thus a primary pathology at this site and not restenosis at a site of previous intimal hyperplasia as might occur following angioplasty. SMC intimal hyperplasia can occur at the more proximal arterial anastomosis and along the graft itself Restenosis after angioplasty can lead to even higher failure rates, from 20 to 50% in the first 6 months following the angioplasty. Stenosis and restenosis both remain major problems after surgery.

To date, numerous methods of treating or preventing intimal hyperplasia have been tested, but none has been clinically satisfactory.

Vascular endothelial growth factor (VEGF) is a naturally-occurring protein. In humans, at least four forms exist, of 121, 165, 189 and 206 amino acids. The cDNA and amino acid sequences of the four forms of human VEGF are given in Houck et al, Molecular Endocrinology (1991) vol 5, No. 12, pages 1806-1814. A partial genomic sequence is also given. The cDNA sequence of human VEGF is also given in Leung et al, Science (1989) 246:1306-1309, together with the bovine VEGF cDNA sequence.

These four forms are referred to herein as VEGF-121, VEGF-165, VEGF-189 and VEGF-206. It should be understood that this numbering refers to the number of amino acids in the mature protein in each case. The translated protein also includes a 26 amino acid presequence which, in nature, is cleaved during intracellular processing.

VEGF is known to play a role in angiogenesis, where it stimulates the division of vascular endothelial cells (EC), increases endothelial permeability and acts as an endothelial "survival factor" in retinal vessels. For example, VEGF, in the form of recombinant protein or when expressed from a plasmid, can induce the development of new blood vessels when injected intra-arterially into ischaemic limbs. This property has led to its use in repairing arteries whose endothelia have been damaged during surgery. Thus, Asahara et al, Circulation (1995) 91: 2793, delivered VEGF, via a cannula, to the interior of rat carotid arteries following angioplasty that had denuded the endothelium of the artery; it was found that VEGF stimulated the reendothelialisation of the artery which, in turn, appeared to contribute to suppression of intimal hyperplasia.

VEGF protein and gene are disclosed in WO-A-9013649, and their use for treating trauma of the vascular epithelium, diabetic ulcers and blood vessel wounds is proposed. VEGF fragments are described in WO-A-9102058, and their use in angiogenesis and re-endothelialisation of inner vascular surfaces, e.g. in the treatment of ulcers.

GB-A-2298577 discloses a non-restrictive, porous, external stent for arteriovenous bypass grafting procedures. This stent has beneficial effects on luminal size and on medial and intimal thickening.

WO-A-9423668 discloses a device for the local delivery of an agent into a blood vessel, including a reservoir formed between two elements thereof. Its use requires implantation, i.e. cutting through the vessel and then securing the device to the vessel walls. The device is partially porous. The reservoir is in direct contact with luminal blood flow. This involves the risk of infection.

U.S. Pat. No. 3,797,485 discloses a device for delivering a drug to the adventitial surface of a blood vessel. It is provided with permanent walls and transcutaneous tubes for the delivery of drug in liquid form. The intention is that the drug should pass to another site.

SUMMARY OF THE INVENTION

The present invention seeks to treat and/or prevent all of the conditions described above, in as much as they arise from intimal hyperplasia. Surprisingly, properties of VEGF have been identified, indicating that it can be used against intimal hyperplasia in different ways.

A collar was placed around the outside of the artery of a rabbit. This procedure normally causes intimal hyperplasia in the rabbit artery, leading to thickening of the arterial wall, which is similar to the stenosis that can occur in human arteries following bypass operations. When the collar was used to deliver DNA encoding VEGF to the arterial wall using a plasmid/liposome vector, the VEGF gene was overexpressed in the arterial wall, including the endothelial layer. Intimal hyperplasia was inhibited. It has been found that the adventitial collar is suitable for arterial gene transfer with all tested gene delivery systems.

This demonstrates that VEGF, in addition to stimulating reendothelialisation in cases where the endothelium is damaged, is capable of suppressing intimal hyperplasia in situations where intimal hyperplasia arises when the endothelium is wholly or largely intact. Therefore, it is potentially useful not only in suppressing restenosis after angioplasty but in preventing or treating de novo stenosis in other surgical situations. There is thus a contrast between the new findings and previous findings, where VEGF was found to stimulate regrowth, or healing, of the endothelium. It is likely that the new findings arise from a different mechanism of action of VEGF.

Furthermore, the new findings demonstrate that effective agents can be delivered to the exterior of the blood vessel, to treat intimal hyperplasia. This has several advantages. In particular, the therapeutic agent is not washed away from the site of the hyperplasia by blood flow as with intralumenal delivery. A delivery reservoir can be maintained around the blood vessel, and there is no need for any intralumenal manipulations which damage the endothelium of the blood vessel (and can themselves trigger intimal hyperplasia).

More particularly, the present invention enables agents for countering SMC intimal hyperplasia to be applied directly to the adventitial surface of the arterial wall (i.e. closest to those cells in the outer media). Any agent used can be applied specifically at the sites most likely to develop an intimal hyperplastic lesion, since these sites are readily exposed at the time of operation.

VEGF mediates its known effects via specific high-affinity tyrosine kinase receptors flk-1/KDR and flt-1 which are only expressed on EC and monocytes. Without wishing to be bound by theory, it is considered likely that the effects of VEGF in the inhibition of hyperplasia are also mediated through the same receptors. Accordingly, the invention also extends to the use of other agonists of the receptors to which VEGF binds, or other materials having the same mechanism of action, to treat or prevent intimal hyperplasia. The specific location of VEGF receptors also confers an advantage of VEGF as compared to many other growth factors and cytokines suggested for the treatment of intimal thickening; the effects of VEGF are more specific to EC since, in the absence of monocytes, high affinity VEGF receptors in the arterial wall are only expressed on EC.

For example, it has been found that the mechanism of VEGF's inhibition of intimal hyperplasia in situations where the endothelium is wholly or largely undamaged is at least partly via the nitric oxide (NO) pathway, as administration of the NO synthesis inhibitor L-NAME counteracts VEGF's effects on intimal hyperplasia in the collar model described above. Thus, VEGF stimulates NO production.

It is also possible that VEGF has other biological effects that contribute to its inhibition of intimal hyperplasia. In particular, it has been found that VEGF overexpression stimulates production of prostacyclin, activation of cytosolic phospholipase $A_2$ and von Willebrand's factor secretion by EC. It may be the case that VEGF's stimulation of NO production and its stimulation of prostacyclin production act in tandem to suppress intimal hyperplasia.

The finding that VEGF acts to stimulate NO and prostacyclin production also suggests that VEGF and agonists of the receptors to which VEGF binds will be useful in the treatment of other NO-linked and/or prostacyclin-linked conditions. In particular, Forte et al, Lancet (1997) 349: 83742, have shown that NO levels are low in individual suffering from hypertension. VEGF may therefore be useful in the treatment of prevention of various forms of hypertension. Similarly, VEGF may be useful in the treatment of atherosclerosis.

According to one aspect of the present invention, an agent that has any of the given characteristics found for VEGF is used for the manufacture of a medicament for the treatment or prevention of intimal hyperplasia, e.g. of stenosis. The agent may be provided in the form of an implant. More particularly, the agent stimulates production of NO or prostacyclin; it may be an agonist of a receptor to which VEGF binds, e.g. VEGF itself or a fragment thereof, or a nucleic acid encoding such an agonist.

According to a second aspect of the invention, a device for use in the delivery of a therapeutic agent to a blood vessel in a patient, comprises a body adapted to provide a seal around the vessel, the agent being held within or associated with the device so that, in use, the agent comes into contact with the adventitial surface of the vessel. Such devices can be biodegradable, and do not require permanent transcutaneous delivery tubes.

DESCRIPTION OF THE INVENTION

As suggested above and demonstrated in the Examples, various agents, including nitric oxide synthase and a nucleic acid encoding it, are suitable for use in the invention. The agent will often be described herein as the VEGF protein or nucleic acid, and those references, and references to VEGF itself, are given by way of example. Any of the forms of VEGF described above may be used for the purposes of this invention.

Herein, references to these VEGF protein sequences are to be understood to refer both to sequences comprising the presequence and sequences lacking the presequence. VEGF proteins with and without the presequence are suitable for the practice of the invention. Similarly, references to VEGF nucleic acid (DNA and RNA) sequences relate to both sequences encoding the presequence and sequences that do not encode the presequence.

It should be noted that Houck et al, supra, give the sequence of VEGF-165 as including the amino acid asparagine (N or Asn) at position 141 (115 in the notation of Houck et al, which corresponds to the mature protein). Houck et al give this amino acid as lysine (K or Lys) in VEGF-121, VEGF-189 and VEGF-206, and the cDNA sequence (of VEGF-206) quoted in Houck et al supports this. Therefore, in the invention, the amino acid at position 141 may be asparagine (N or Asn) or lysine (Lys or K). Each amino acid is encoded by the appropriate triplet codon in nucleic acid sequences of the invention (for DNA, these codons may be AAA or AAG for lysine and AAT or AAC for asparagine). This applies especially to VEGF-165.

The four forms are encoded by the same gene but generated by alternative splicing at the RNA level. Thus, there is a full-length form of human VEGF and three known truncated forms. VEGF-121 and VEGF-165 are soluble and are secreted forms. Similarly, the 26 amino acid presequence is hydrophobic and is believed to decrease the solubility of the protein. Thus, forms of VEGF without the presequence are preferred, as they are expected to have higher solubility. All forms of VEGF are suitable for the practice of the invention, though secreted forms are preferred. VEGF proteins suitable for the practice of the invention may also originate from other species, although human VEGF is preferred. For example, mouse, rabbit and cow VEGF have been cloned and their sequences are available.

For reference, it should be noted that VEGF-121, 165, 189 and 206 are also referred to in the art as VEGF-120, 164, 188 and 205.

VEGF proteins and nucleic acids (DNA and RNA) are suitable agents for the practice of the invention.

When VEGF protein is used, VEGF protein having the amino acid sequence of SEQ ID No. 2 (VEGF-121), 4 (VEGF-165), 6 (VEGF-189) or 8 (VEGF-206) is preferred. Secreted forms of VEGF are preferred, and so VEGF-121 and VEGF-165 are particularly preferred.

In the practice of the invention, it is preferred to use VEGF DNA encoding VEGF-121, VEGF-165, VEGF-189 or VEGF-206, e.g. having the sequence of SEQ ID No. 1, 3, 5 or 7. DNA sequences encoding secreted forms of human VEGF are preferred. Thus, DNA sequences of SEQ ID No. 1 and 3 are particularly preferred.

However, the VEGF DNA and proteins suitable for the practice of the invention are not limited to those specific sequences. Rather, the invention also provides for the use of other closely related DNA and protein sequences.

DNA sequences of the invention may be related to that of SEQ ID No. 1, 3, 5 or 7 in a number of ways. For example, DNA sequences suitable for the practice of the invention may be degenerate sequences that encode the same protein, the protein of SEQ ID No. 2, 4, 6 or 8.

Alternatively, DNA sequences of the invention may be substantially homologous to that of SEQ ID No. 1, 3, 5 or 7, and encode a protein that differs in amino acid sequence from that of SEQ ID No. 2, 4, 6 or 8 but encodes a protein having VEGF activity. Typically, DNA sequences for use in the invention have at least 70%, at least 80%, at least 90%, at least 95%, or at least 99% sequence homology to the sequence of SEQ ID No. 1, 3, 5 or 7.

Similarly, VEGF DNA sequences for use in the invention may encode fragments of VEGF that retain VEGF activity. Fragments of interest are, say, at least 15 amino acids long, e.g. up to 40 or more amino acids. Examples of suitable fragments are 20 amino acids long, e.g. the sequences 1-20, 11-30, 21-40, 31-50, 41-60, 51-70, 61-80, 71-90, 81-100, 91-110, 101-120, 111-130, 121-140, 131-150, 141-160, 151-170, 161-180, 171-190, 181-200, 191-210 and 196-215 of the active VEGF protein shown as SEQ ID No. 6.

DNA sequences for use in the invention may, for example, be genomic DNAs or cDNAs, or hybrids between genomic DNA and cDNA, or they may be synthetic or semisynthetic. They may originate from any species, though DNAs encoding human VEGF are preferred. They may be single-stranded or double-stranded. Genomic DNAs encoding the proteins of SEQ ID. No. 2, 4, 6 and 8 are particularly preferred.

DNA sequences for use in the invention may differ from the sequence shown in SEQ ID No. 1, 3, 5 or 7 by the deletion, insertion or substitution of one or more nucleotides, provided that they encode a protein having VEGF activity. Similarly, they may be truncated with respect to SEQ ID No. 1, 3, 5 or 7 or extended by one or more nucleotides provided that they encode a protein having VEGF activity.

RNA sequences are also suitable for the practice of the invention. In particular, the invention provides for the use of the RNA sequences corresponding to those of SEQ ID No. 1, 3, 5 or 7; these are preferred RNA sequences. The invention also provides for the use of RNA sequences that are related to these sequences in any of the ways described above for DNA sequences. RNA sequences for the invention may be single-stranded or double-stranded. RNAs of the invention may be of any origin. For example, they may originate from any species, although RNAs encoding human VEGF, especially human VEGF having the sequence shown in SEQ ID. No. 2, 4, 6 or 8 are preferred. Synthetic DNAs may also be used, as may semi-synthetic RNAs. Further, DNA transcribed form bacterial plasmids in vivo or in vitro may be used.

It will be appreciated by those of skill in the art that, in RNA sequences suitable for the practice of the invention, the T residues will be replaced by U.

VEGF proteins for use in the invention are encoded by DNA or RNA sequences of the invention as defined above. Preferred proteins of the invention are the proteins of SEQ ID No. 2, 4, 6 and 8 though the invention also provides for the use of other proteins having closely related sequences that differ from those of SEQ ID No. 2, 4, 6 or 8 but have VEGF activity.

According to the invention, insofar as it relates to the treatment or prevention of intimal hyperplasia, VEGF activity is the ability completely or partially to inhibit or prevent intimal hyperplasia in a blood vessel, particularly an artery. Proteins that differ slightly in sequence from naturally-occurring VEGF, as described above, retain this property, although not necessarily to as great an extent as VEGF. Similarly, such proteins may exhibit stronger VEGF activity than naturally-occurring VEGF. The same applies to agonists of VEGF, for example peptide, peptoids or other small molecules.

Insofar as the invention relates to other properties of VEGF, VEGF activity is the ability of molecules other than VEGF to reproduce those properties. For example, insofar as the invention relates to VEGF's activity against NO-linked conditions to stimulate NO production, VEGF activity includes the ability to stimulate NO production. Insofar as the invention relates to VEGF's activity against prostacyclin-linked conditions, VEGF activity includes the ability to stimulate prostacyclin production. VEGF proteins suitable for the practice of the invention also typically exhibit one or more of the biological properties of VEGF that are already known in the art, such as the ability to promote the proliferation of arterial EC in vitro and/or in vivo or the ability to bind to the receptors to which VEGF binds and activate them in the manner of VEGF.

VEGF proteins suitable for the practice of the invention may be substantially homologous to the VEGF of SEQ ID No. 2, 4, 6 or 8, typically at least 70%, at least 80%, at least 90%, at least 95%, or at least 99% homologous.

VEGF proteins suitable for the practice of the invention may differ from the sequence shown in SEQ ID No. 2, 4, 6 or 8 by the deletion, insertion or substitution of one or more amino acids, provided that they have VEGF activity. Similarly, they may be truncated by one or more amino acids with respect to SEQ ID No. 2, 4, 6 or 8 or extended with respect to SEQ ID No. 2, 4, 6 or 8 by one or more amino acids, provided that they have VEGF activity. In respect of substitutions, conservative substitutions are preferred. Typically, conservative substitutions are substitutions in which the substituted amino acid is of a similar nature to the one present in naturally-occurring VEGF, for example in terms of charge and/or size and/or polarity and/or hydrophobicity. Similarly, conservative substitutions typically have little or no effect on the VEGF activity of the protein.

VEGF proteins for use in the invention that differ in sequence from naturally-occurring VEGF may be engineered to differ in activity from naturally-occurring VEGF. For example, they may be engineered to have stronger VEGF activity. Such manipulations will typically be carried out at the nucleic acid level using recombinant techniques known in the art.

As an alternative to using a VEGF protein as described above, it is possible to use a VEGF agonist. This applies to all the medical applications described herein, especially the treatment of atherosclerosis.

In general, a VEGF agonist is a molecule which binds to a receptor to which VEGF binds and has substantially the same effects, leading to VEGF activity, as described herein. In particular, an agonist may bind to the flk-1/KDR or flt-1 receptors. Agonists of the invention are thus referred to both as agonists of VEGF and of the receptors to which VEGF binds.

A VEGF agonist may have any chemical structure. For example, a VEGF agonist may be peptide or polypeptide of, for example, up to 10, up to 20, up to 50 or up to 100 amino acids. An agonist may similarly be a modified peptide, or a peptoid. Any suitable modification may be made, including glycosylation, sulphation, COOH-amidation and acetylation, e.g. N-terminal acetylation. Additionally, or alternatively, modified amino acids and/or L-amino acids may be present.

Some preferred agonists are fragments, optionally modified as described above, of VEGF, that have VEGF activity. One particularly preferred agonist fragment of VEGF consists of amino acids 1 to 20 (M . . . H) of SEQ ID No. 4; this peptide is reported to be an agonist of the Flt-1 receptor in human trophoblast cells, by Ahmed et al, Lab. Invest. (1997) 76:779.

Additional related agonists may also be derived from the N-terminal region of VEGF. For example, with reference to SEQ ID No. 4, peptide agonists of VEGF may comprise the N-terminus of VEGF (amino acid No. 1) and have the amino acid sequence of VEGF up to an amino acid in the range of 25 to 30, 30 to 40, 40 to 50 or 50 to 100. Similarly, preferred agonists may be derived from the N-terminal region of VEGF but comprise a truncated version of the N-terminus. For example, instead of beginning at amino acid No. 1 in SEQ ID No. 4, they may begin at amino acid No. 2, 3, 4, 5, 6, 7, 8, 9 or 10 of SEQ ID No. 4, and have the amino acid sequence of VEGF up to an amino acid in the range of 25 to 30, 30 to 40, 40 to 50 or 50 to 100.

Peptide agonists of the invention may also be derived from other parts of the VEGF sequence. For example, a further preferred peptide agonist is a peptide consisting of amino acids 145 to 169 (R . . . P) of the VEGF-189 sequence of SEQ ID No. 6.

Additional related agonists may also be derived from this region of VEGF. For example, with reference to SEQ ID No. 6, peptide agonists of VEGF may have the amino acid sequence of VEGF from an amino acid in the region of 135 to 155 to an amino acid in the region of 160 to 180. For example, peptide agonists derived from this region may have the sequence of VEGF from an amino acid in the region of 135 to 140, 140 to 145 or 145 to 150 to an amino acid in the region of 160 to 165, 165 to 170 or 170 to 175.

Peptide fragments of VEGF as defined above preferably have a total length of 10 to 20, 20 to 25, 25 to 30, 30 to 40 or 40 to 50 amino acids.

Other preferred agonists are fragments of the HIV Tat protein. The HIV Tat protein mimics the agonist actions of VEGF and can stimulate angiogenesis in endothelial cells acting through the Flk-1/KDR receptor; see Albini et al, Oncogene (1996) 12:289-297, and Nature Medicine (1996) 2(12):1321-1375. Thus, peptides derived from the HIV-1 Tat sequence such as the amino acids 46-60 of HIV Tat protein have been shown to stimulate growth and migration of endothelial cells; see Albini et al, Oncogene (1996) 12:289-297. The peptide consisting of amino acids 41 to 65 of HIV-1 Tat protein is a further preferred peptide agonist of the invention.

Agonists of the invention may also have amino acid sequences that differ from that of naturally-occurring VEGF in any of the ways described above for VEGF proteins, as long as their agonist properties are retained.

Where the agonists of the invention are peptides, they may be generated in vivo from nucleic acid sequences encoding them, in order to effect treatment according to the invention. Thus, agonist-encoding nucleic acids may be delivered by gene therapy, as described herein.

Alternatively, non-peptide VEGF agonists can be used. For example, small molecules that mimic the shape of the parts of VEGF that interact with its receptors may be used.

In the practice of the invention, VEGF, a nucleic acid encoding VEGF or a VEGF agonist or nucleic acid encoding a VEGF agonist may be delivered to a blood vessel, preferably an artery in any suitable form. Nucleic acids may be delivered in a "naked" form unassociated with a vector, or by means of a gene therapy vector. It is preferred to deliver them by means of any suitable gene therapy vector. In particular, viral or non-viral vectors may be used.

Suitable viral vectors include adenoviruses, retroviruses, pseudotyped retroviruses, herpesviruses, vaccinia viruses and baculoviruses. Suitable non-viral vectors include oligonucleotides, plasmids, liposomes, cationic liposomes, pH-sensitive liposomes, liposome-protein complexes, immunoliposomes, liposome-protein-polylysine derivatives, water-oil emulsions, polyethylene imines and dendrimers. Preferred vectors include Moloney murine leukaemia virus (MMLV)-derived retroviruses, pseudotyped vesicular stomatitis virus protein-G (VSV-G)-containing retroviruses, adenoviruses, plasmids and plasmid/liposome complexes.

Where appropriate, two or more types of vector can be used together. For example, a plasmid vector may be used in conjunction with liposomes. Suitable liposomes include, for example, those comprising dioleoylphosphatidylethanolamine (DOPE), 3β-[N-(N',N'-dimethylaminoethane)carbamoyl]cholesterol (DC-Chol), or the positively-charged lipid (N-[1-(2,3-dioleyloxy)propyl]-N,N,N-triethylammonium (DOTMA).

Viral vectors of the invention are preferably disabled, e.g. replication-deficient. That is, they lack one or more functional genes required for their replication, which prevents their uncontrolled proliferation in vivo and avoids undesirable side-effects of viral infection. Preferably, all of the viral genome is removed except for the minimum genomic elements required to package the viral genome incorporating the VEGF nucleic acid into the viral coat or capsid. For example, it is desirable to delete all the viral genome except the Long Terminal Repeats (LTRs) and a packaging signal. In the case of adenoviruses, deletions are typically made in the E1 region and optionally in one or more of the E2, E3 and/or E4 regions.

Viruses of the invention may be disabled by any suitable technique. For example, genomic deletions may involve complete removal of genes required for replication, or only partial removal. Complete removal is preferred. In general, preferred deletions are of genes required for early transcription of viral genes.

Replication-competent self-limiting or self-destructing viral vectors may also be used.

In general, the VEGF nucleic acid for use in the invention will be comprised within an expression construct that ensures their expression in vivo after they have been delivered to the artery, preferably by a vector as defined above. Such constructs typically comprise a promoter capable of directing the expression of the VEGF nucleic acid (and optionally a regulator of the promoter), a translational start codon and, operably linked to the promoter, the VEGF nucleic acid. Preferably, these components are arranged in a 5'-3' orientation.

The construct may also comprise any other suitable components. For example, the construct may comprise a nucleic acid encoding a signal sequence, so positioned in such a position relative to the VEGF nucleic acid that, when it is translated, it is capable of directing the expressed VEGF protein to a given cell type or cell compartment. Any such signal sequence will typically be positioned immediately 3' or immediately 5' to the VEGF nucleic acid, such that the signal sequence and VEGF protein are translated as a single fusion protein, with the signal sequence at the C- or N-terminus.

The construct may also comprise an enhancer which enhances the degree of expression provided by the promoter. Any enhancer which enhances the expression provided by the selected promoter may be used. For example, in the case of the CMV early gene promoter, the CMV early gene enhancer may be used.

Optionally, the construct may comprise a transcriptional terminator 3' to the VEGF nucleic acid. Any suitable terminator may be used.

Optionally, the construct may comprise a polyadenylation signal operably linked 3' to the VEGF nucleic acid.

Optionally, the construct may comprise one or more selectable marker genes, e.g. of antibiotic-resistance, to allow selection of transformed cells in culture. For example, cells may be selected for antibiotic resistance in order.

Optionally, the construct may comprise one or more introns, or other non-coding sequences, for example 3' or 5' to the VEGF nucleic acid.

Any suitable promoter may be used to control the expression of the nucleic acid of the invention. In general, it is preferred to use a viral promoter or a promoter adapted to function in the species of the subject to be treated. Thus, in the case of a human subject, it is preferred to use viral promoters, especially promoters derived from viruses that infect humans, or promoters derived from human genes. Optionally, a promoter may be used in combination with any suitable enhancer.

Desirably, a "strong" promoter is used, i.e. one that secures high levels of expression of the VEGF protein of the invention. Promoters that achieve overexpression of the VEGF protein are desirable. Preferred promoters include the cytomegalovirus (CMV) promoter, optionally in combination with the CMV enhancer, the human β-actin promoter; the simian virus 40 (SV40) early gene promoter; the Rous sarcoma virus (RSV) promoter; and the retroviral long terminal repeat (LTR) promoter.

Promoters, and other construct components, are operably linked to the VEGF nucleic acid. Thus, they are positioned in order that they may exert their effect on expression of the VEGF nucleic acid. For example, in the case of a promoter, the promoter is positioned relative to the VEGF nucleic acid such that it is able to direct expression of the VEGF nucleic acid. Desirably, construct components are positioned to allow them to exert their maximum effect on expression.

The nucleic acids or constructs use in the invention, may be incorporated into viral genomes by any suitable means known in the art. Viral genomes may then be packaged into viral coats or capsids by any suitable procedure. In particular, any suitable packaging cell line may be used to generate viral vectors of the invention. These packaging lines complement the replication-deficient viral genomes of the invention, as they include, typically incorporated into their genomes, the genes which have been deleted from the replication-deficient genome. Thus, the use of packaging lines allows viral vectors of the invention to be generated in culture. Suitable packaging lines include derivatives of PA317 cells, Ψ-2 cells, CRE cells, CRIP cells, E-86-GP cells, Fly cells, line 293 cells and 293GP cells.

In the case of non-viral vectors, nucleic acid may be incorporated into the non-viral vectors by any suitable means known in the art.

As desired, vectors, especially viral vectors, may be selected to achieve integration of the nucleic acid or construct into the genome of the cells of the subject to be treated, or to leave the nucleic acid or construct free in the cytoplasm. Integrative vectors are preferred.

VEGF proteins or VEGF nucleic acids for use in the invention, preferably associated with a viral or non-viral vector, as described above, may be administered to arteries in any suitable manner in order to effect treatment of hyperplasia. For example, VEGF or a nucleic acid encoding VEGF may be administered to the exterior wall of the blood vessel, e.g. artery, or to the blood vessel endothelium, e.g.

the arterial endothelium, for example via the lumen. Local gene transfer is likely to be advantageous over the administration of recombinant VEGF protein since infused compounds are rapidly flushed away by blood flow and short half-life in blood.

Once delivered, VEGF nucleic acids of the invention are expressed to produce VEGF proteins, which in turn effect treatment or prevention of intimal hyperplasia. Expression may take place in any cell type or types in the blood vessel, e.g. arterial, wall.

Preferably, expression occurs in such a location that the expressed VEGF is able to reach the endothelium of the blood vessel, e g. artery. For example, expression may occur in the smooth muscle cells and/or in the endothelium. Most preferably, expression takes place at least in the endothelium of the blood vessel, e g. artery.

For example, VEGF protein or nucleic acid may be delivered to the outside of the blood vessel, e.g. artery, by direct injection around the site of the hyperplasia to be treated or prevented, or by injection into the lumen of the blood vessel, e.g. artery.

More preferably, the VEGF protein or nucleic acid is delivered by means of an implant placed externally to the blood vessel, e.g. artery, in proximity to the site of the hyperplasia to be treated. Such an implant contains the VEGF protein or nucleic acid or the vector and provides a reservoir of the agent. The VEGF protein or nucleic acid (preferably in association with a vector) may be introduced into the implant before or after the implant is introduced into the subject to be treated. For example, the implant may be fitted in the vicinity of the blood vessel, with the VEGF protein or nucleic acid being introduced into the implant, e.g. by injection, subsequently.

Preferably, the implant is placed in direct contact with the blood vessel, e.g. artery. This is especially preferred when retroviral vectors are used to deliver VEGF nucleic acids, as the physical distortion of the blood vessel may induce smooth muscle cell proliferation, which increases the efficiency of gene transfer by retroviral vectors. This proliferation, like the proliferation induced by the hyperplasia itself, is overcome or at least ameliorated, by the delivery of the VEGF protein or nucleic acid. Similarly, it is preferred for the implant to be in contact with the artery when employing other vectors that exhibit increased efficiency of gene transfer when their target cells are dividing. For example, cell proliferation may also enhance gene transfer efficiency with plasmid/liposome complexes.

Such implants may be in any suitable form. Preferably, the implant is in the form of a collar which surrounds, partially or completely, preferably completely, the artery, at or near the site of the hyperplasia to be treated or prevented.

Extravascular gene delivery avoids procedures such as balloon catheterization or high pressure fluid which may lead to endothelial damage or denudation. Transfected genes are preferably applied via a silastic or biodegradable implant, preferably a collar placed next to, preferably around, the outside of the blood vessel. The endothelium suffers little or no damage. This is a major advantage of this form of delivery.

When, according to the invention, vectors are applied directly on the adventitial surface of a blood vessel within a collar, close contact with the adventitia is maintained. In rabbit arteries, a collar alone typically leads to the formation of a neointima within 7-14 days after the operation. The collar also maintains a high concentration of vector at the adventitial surface.

Implants, preferably collars, may be made of any suitable material. Silastic implants, i.e. implants comprising silicone rubbers, are one preferred alternative. Most preferred are biodegradable implants. Any suitable biodegradable material may be used.

Within the implant, e.g. collar, the VEGF protein or nucleic acid may be contained in any way. Preferably, the structure of the implant, e.g. collar, is such that the VEGF protein or nucleic acid is held in direct contact with the blood vessel wall. Thus, in one embodiment, the structure of the implant leaves a space between the blood vessel wall and the wall of the implant. In the case of a collar, the implant thus forms a hollow container around the blood vessel. Into this space, VEGF nucleic acids or proteins can be introduced, such that they are in contact with the blood vessel wall. Preferably, the extremities of the implant are in contact with the blood vessel wall, thus preventing the escape of the VEGF nucleic acid or protein. Preferably, the outer wall of the collar is impermeable, or substantially impermeable, to the VEGF nucleic acid or protein, thus preventing, or at least limiting, its escape into the surrounding tissue and ensuring its delivery to the blood vessel.

Optionally, the space containing the VEGF nucleic acid or protein may be separated from the wall of the blood vessel by one or more layers of material permeable or semi-permeable to the VEGF or nucleic acid. This may be desirable if gradual delivery is intended and is desired to limit the rate at which VEGF protein or nucleic acid is delivered to the blood vessel wall.

Optionally, the implant, e.g. collar, may be designed to act as an osmotic pump.

Optionally, the VEGF may be contained within a medium within the collar, e.g. a solid or gel medium. This may help to prevent the VEGF protein or nucleic acid escaping into the tissue. In this case, the outer wall of the collar may not need to be in contact with the blood vessel of the extremity of the implant.

Alternatively, the VEGF nucleic acid or protein may be coated onto the surface of the implant which is in contact with the blood vessel in use. Alternatively, the VEGF nucleic acid or protein may be dispersed throughout the structure of the implant.

Some advantages of the use of implants in this way, especially collars, are: (i) they provide a delivery reservoir, allowing for sustained delivery; (ii) no intralumenal manipulations are required and the arterial endothelium remains intact; and (iii) the distortion (e.g. constriction in the case of a collar) created by the implant may enhance the efficiency of gene delivery, as explained above.

A device of the invention generally comprises a body including at least a first substantially impermeable body portion which is shaped to in use extend longitudinally along and at least partially surround a first blood-carrying vessel, the first body portion including longitudinally spaced apart seal portions adapted to seal in use against the adventitial surface of the first blood-carrying vessel, and an intermediate portion between the seal portions which is adapted to in use contain and deliver the at least one agent to the adventitial surface of the first blood-carrying vessel.

Preferred embodiments of devices in accordance with the present invention will now be described, by way of example only, with reference to the accompanying drawings, in which:

FIG. 9 is a longitudinal cross-sectional view in the vertical plane of the embodiment of FIG. 8;

FIG. 10 shows in perspective a schematic view of a fifth embodiment of a device positioned around a side-to-side anastomosis, showing a part-embedded blood vessel; and FIG. 11 is a longitudinal cross-sectional view in the vertical plane of the embodiment of FIG. 10.

Figure 4:
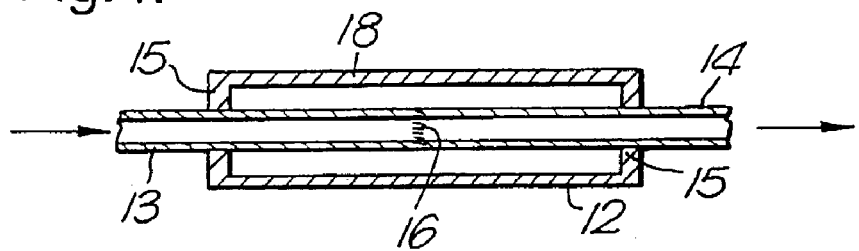
FIG. 4 is a longitudinal cross-sectional view in the vertical plane of the embodiment of FIG. 3.

By way of background, arterial bypass grafts are commonly used to restore or improve the blood flow to tissues when the native vessels are occluded or significantly stenosed, usually by atheroma. Whether using autologous vein or artery, or a synthetic material such as Dacron or PTFE, grafts are commonly anastomosed to the native vessels in one of three ways: "end-to-end" (FIG. 4); "end-to-side" (FIG. 7); or "side-to-side" (FIG. 9). Of these techniques, end-to-side and side-to-side are much more common than end-to-end. The direction of blood flow is represented by the arrows.

Figure 1:
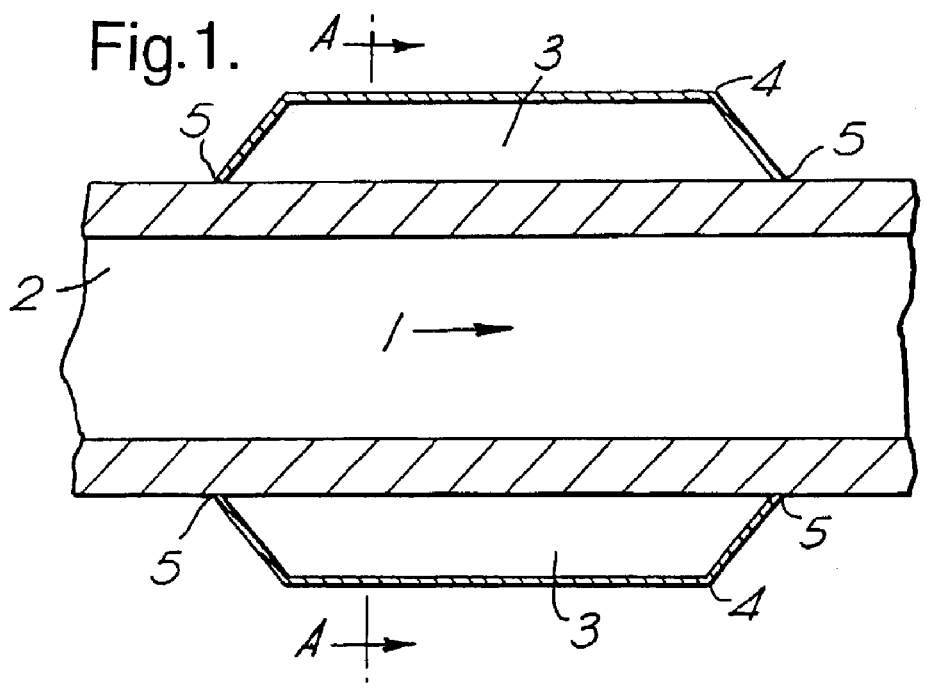
FIG. 1 is a schematic, longitudinal sectional view of a device of the invention in place around a blood vessel.
Figure 2:
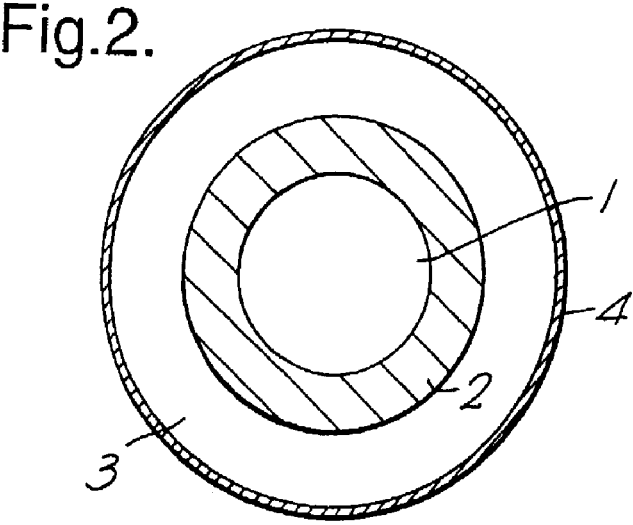
FIG. 2 is a schematic, coronal sectional view of the same embodiment, along the line A-A shown in FIG. 1.

FIGS. 1 and 2 show blood 1 within a vessel wall 2, and an adventitial collar including a void space 3 defined by a wall 4, e.g. of a biodegradable material. A collar 5 touches the vessel wall at the collar's extremities. This embodiment may be used in the same manner as is described below, for other embodiments.

Figure 3:
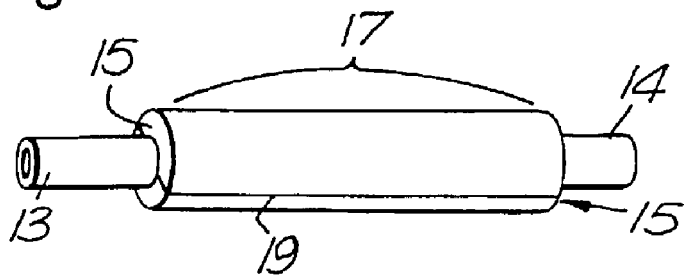
FIG. 3 shows in perspective a schematic view of a second embodiment of a device positioned around an end-to-end anastomosis.

The embodiment illustrated in FIGS. 3 and 4 is shown applied to an end-to-end anastomosis. The device comprises a generally tubular body 12 which, in use, extends longitudinally along and surrounds the blood-carrying vessel made up by the end-to-end anastomosis of a graft 13 to a native blood vessel 14.

As is most clearly visible from FIG. 4, the body 12 of the device has longitudinally spaced-apart seal portions 15 provided at its opposite ends. When, in use, the device is positioned over the site 16 of the end-to-end anastomosis, these seal portions 15 seal against the adventitial surface of the graft 13 and native blood vessel 14. The radial thickness of the material of the body 12 is greater at the seal portions 15 than it is in an intermediate portion 17. Consequently, when the seal portions 15 seal against the adventitial surfaces of the graft 13 and vessel 14, a space is formed between the interior of the body 12 of the device and the adventitial surfaces of the enclosed ends of the graft 13 and vessel 14. This space constitutes a sealed reservoir 18 and is shown longitudinally aligned with the anastomosis 16.

This reservoir enables a pharmaceutical formulation containing one or more agents to be placed in contact with the adventitial surface of the graft and vessels 13,14 at the site of the anastomosis 16. Where the formulation is in the form of a fluid or gel it can for example be injected using a hypodermic needle and syringe, through the wall of the body 12, into the sealed reservoir 18. The agents contained in the formulation advantageously have an anti-proliferative effect, to counter smooth muscle cell intimal hyperplasia at the site of the anastomosis 16 and areas contiguous to it.

The pharmaceutical formulation need not be in fluid or gel form, for example it may be a runny paste having a consistency similar to that of toothpaste. It then remains in contact with the pulsing adventitial surface to which it is exposed, constricting the vessel.

To position the device over the site of the anastomosis 16, the cylindrical body 12 may be slid axially over one of the graft 13 and blood vessel 14 prior to their being anastomosed. The surgeon can then join the graft 13 and vessel 14 together at the anastomosis site 16 and the body 12 may then be slid back over the anastomosis site 16 to occupy the position shown in FIG. 4, to enable sealing of the seal portions 15 to the respective adventitial surfaces.

Alternatively, the body 12 of the device may, as shown, be provided with a longitudinal slit 19 along its full length. In this way, the surgeon can anastomose the graft 13 and vessel 14 without introducing the device 12 to the patient's body. Once the anastomosis has been successfully completed, the surgeon can then select an appropriately sized body 12 and apply it around the anastomosed graft and vessel by opening the flexible body 12 along slit 19, slipping it over the anastomosed graft and vessel 13,14 and then sealing the opposed longitudinal edges of the body at the slit 19 together, for example using a conventional "tissue glue", such as the thrombin glue sold under the name Tisseal, or a cyanomethacrylate-based glue.

To concentrate the effect of the pharmaceutical formulation contained within the reservoir 18, and to avoid leakage of its agents to the surrounding tissue, the body 12 is substantially impermeable to the formulation. The material is also, advantageously, biodegradable over a set time course, for example a period of 1 to 5 days, by which time the active agents in the formulation are likely to have become exhausted. The material is also chosen so as not to promote too severe a reaction from the surrounding tissue. Examples of suitable materials for the body include gelatin, alginate or collagen. These materials also allow the body flexibility and enable the device to be manufactured by molding or extrusion.

The wall material of the body 12 may also advantageously be self-sealing, so as to preserve the integrity of the sealed reservoir 18 if it is required to be punctured by a hypodermic needle. Alternatively or additionally, any leak in the wall that is revealed after removal of the needle may be sealed with "tissue glue" or the like.

A range of differently sized bodies 12 may be provided to be fitted over differently sized vessels. Lower limb vessels commonly have an external diameter of approximately 6-8 mm. Coronary vessels commonly have an external diameter of approximately 3-5 mm. Accordingly, a range of body sizes of between about 3-10 mm diameter may be made available in sterilised packets to the surgeon. In addition, the size of the body may be varied to influence the volume of the reservoir 18. A suitable size for the reservoir 18 is up to 10 ml, preferably 2-5 ml.

To accommodate expansion of the blood-carrying vessel 13,14 caused by pulsatile blood flow therealong, at least the seal portions 15 of the body are advantageously capable of being stretched so as to accommodate expansion of the vessel walls. It is highly desirable to avoid constriction of the vessel walls by the device, whilst at the same time maintaining the seals intact.

Figure 5:
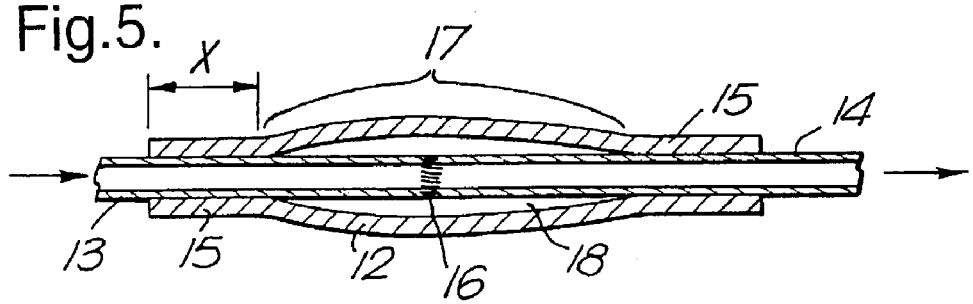
FIG. 5 is a similar view to that of FIG. 4, but showing a modified form of that embodiment; with an alternative construction for its seal portions.

FIG. 5 illustrates different seal portions. The radial thickness of the material of the body 12 is constant along the length of the body, and the intermediate portion 17 is ballooned internally relative to the internal diameter of the body 12 at the seal portions 15. Both seal portions 15 are formed with tails which extend in the longitudinal direction, for example each to contact the respective adventitial surfaces of the graft 13 and vessel 14 over a length "X" in the axial direction, of approximately 8-15 mm. These long tails for the seal portions 15 can be made to act in the manner of "flap valves" to help seal the reservoir 18, although clearly no flow through the "flap valve" is desired. Alternatively, the tails may be folded inwardly (not shown) to double the thickness of the body at its ends to form seal portions of greater radial body thickness than the body thickness in the intermediate portion, in a fashion similar to that shown in FIG. 4.

To form or help form fluid-tight seals, the surgeon may adhere the seal portions 15 to the adventitial surfaces, for example using a glue of the type mentioned above, for example a "tissue glue". This may not, however, be essential. For example, if the size of the body 12 at the seal portions 15 is chosen to match the girth of the vessels 13,14, it may not be necessary to use any glue. Instead, the surgeon might rely on the radial interference between the internal diameter of the body 12 at the seal portions 15 and the diameter of the adventitial surfaces. This is particularly so with the long-tailed seal portion embodiment of FIG. 5. The seal portions should not, however, be so tight on the vessel as to constrict it.

Figure 6:
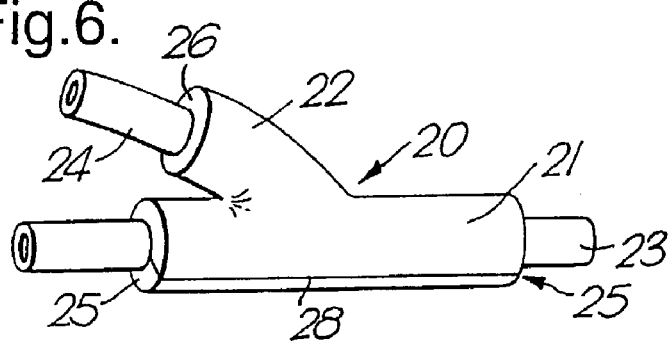
FIG. 6 shows in perspective a schematic view of a third embodiment of a device positioned around an end-to-side anastomosis.
Figure 7:
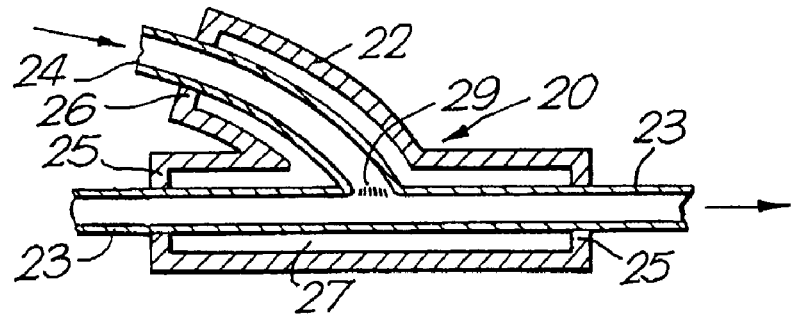
FIG. 7 is a longitudinal cross-sectional view in the vertical plane of the embodiment of FIG. 6.

FIGS. 6 and 7 illustrate an embodiment of the device that is used in conjunction with an end-to-side anastomosis. These drawings show a body 20 having a first body portion 21 and a second body portion 22 branched thereto at an angle of less than 90° to form a generally Y-shaped body. It will be appreciated that the first and second body portions 21,22 may be branched to one another at other branch angles up to and including 90°, in which latter case the body be generally T-shaped. The surgeon may advantageously have available to him a series of differently sized and differently shaped bodies from which he may choose the device most appropriate to the layout and size of the anastomosed vessels. The first body portion 21 may, for example, be approximately 1-10 cm in length; the second body portion 22 may be 1-5 cm in length.

The first body portion 21 is generally tubular and is shown as surrounding a native blood vessel 23. The second body portion 22 is also generally tubular and is shown as surrounding a graft 24 anastomosed to the native blood vessel 23 in end-to-side fashion at anastomosis site 29. As can be seen from FIG. 7, the opposite ends of the first body portion 21 are provided with seal portions 25 and the extreme end of the second body portion 22 is provided with a seal portion 26. As in the earlier embodiment, these seal portions 25,26 may advantageously be sealed to the adventitial surfaces of the blood vessel 23 and graft 24 respectively using a "tissue glue".

FIG. 7 shows a sealed reservoir 27 formed between the interior of the first body portion 21 and the adventitial surface of the blood vessel 23. The reservoir 27 extends into the interior of the second body portion 22. This sealed reservoir 27 is thus aligned with the site 29 of the anastomosis. The reservoir 27 may advantageously be injected with a liquid pharmaceutical formulation containing active agents, using a hypodermic needle and syringe.

To facilitate fitment of the device to the vessel 23 and graft 24, the body 20 of the device may be provided to the surgeon in a sterilised package containing two symmetrical halves, split in and symmetrical about the plane of the section illustrated in FIG. 7. In such a case, the surgeon would be required to assemble the two identical body halves together after having anastomosed the graft 24 to the vessel 23, and to seal the facing edges of the identical halves together, for example using glue as previously described.

Alternatively, only the first body portion 21 may be provided with a longitudinal slit 28, as shown in FIG. 6. In this way the surgeon could slide the second body portion 22 over the end of the graft 24. The surgeon would then be able to anastomose the free end of the graft 24 to the blood vessel 23 and then slide the second body portion 22 back down the graft 24 to cover the site of the anastomosis 29, using the slit 28 to feed the blood vessel 23 into the centre of the first body portion 21 to be surrounded thereby. The surgeon could then seal to one another the facing longitudinal edges of the first body portion 21 at the slit 28 to form the sealed reservoir 27 therein.

It will be appreciated that other configurations may be used for the body portions 21 and 22. For example, the first and second body portions 21 and 22 could be provided separately from one another and be secured to one another to form the sealed reservoir 27 only when in situ in the patient.

Figure 8:
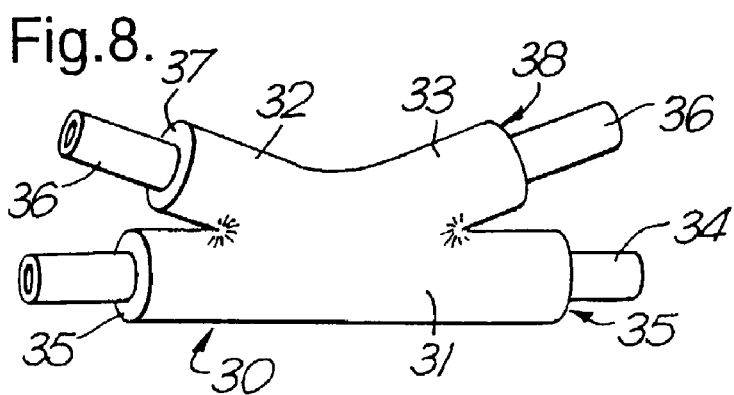
FIG. 8 shows in perspective a schematic view of a fourth embodiment of a device positioned around a side-to-side anastomosis.

FIGS. 8 and 9 illustrate an embodiment of device suitable for use in the situation of a side-to-side anastomosis. The body 30 of the device is shown as comprising a first body portion 31, from which are branched second and third body portions 32,33. The branching forms a generally X-shaped body as shown in FIG. 8.

All three body portions 31,32,33 are generally tubular in shape. The device is generally similar to that illustrated in FIGS. 6 and 7, save for the additional third body portion 33.

First body portion 31 surrounds the occluded native blood vessel 34 and is sealed to the adventitial surface thereof by seal portions 35. Second and third body portions 32,33 surround the graft 36 and are sealed to the adventitial surface of the graft at respective seal portions 37,38. As is most clearly shown in FIG. 9, the effect of the seal portions 35,37,38 is to form a sealed reservoir 39 between the interior of the body 30 and the adventitial surfaces of the enclosed vessels, which reservoir 39 can be at least part-filled with a pharmaceutical formulation in the manner described earlier.

To facilitate fitment of the device illustrated in FIGS. 8 and 9, the device is advantageously provided to the surgeon in at least two parts. For example, the first body portion 31 may be provided separately from a second component comprising second and third body portions 32,33. By providing the body portions with longitudinal slits (not shown), the body portions may be fitted to surround the vessel 34 and graft 36 and then be sealed along those longitudinal slits and sealed to one another along a line of contact, to provide the sealed reservoir 39 around the point of anastomosis 40.

FIGS. 10 and 11 show a variant of the device shown in FIGS. 8 and 9 (and use the same reference numerals for common parts). One particularly suitable use for the device of the present invention is in coronary artery bypass graft surgery. In such a situation, the first blood vessel 34 may, as shown, be a coronary artery that is part-embedded in the heart wall 50. A device of the form shown in FIGS. 8 and 9 could not be fitted to a part-embedded coronary artery 34, as the first body portion would be unable to extend fully around the artery 34. Accordingly, in the embodiments of FIGS. 10 and 11, the first body portion 51 of the body 31 does not describe a full circle when viewed in cross-section transverse to its longitudinal extent; instead, it is generally arcuate. In the illustrated embodiment it describes an arc of approximately 180°. This enables the first body portion 51 to be fitted over only the exposed portion of the part-embedded coronary artery 34, to surround it only partly. In this arrangement, the longitudinally-extending edges 41 of the first body portion 51 are sealed by the surgeon either to the adventitial wall of the coronary artery 34 or, as shown, to the surface of the heart wall 50, for example by using tissue glue.

The device of FIGS. 10 and 11 is also applicable to other surgical procedures in which the first blood-carrying vessel is an artery part-embedded in a wall of the organ supplied by that artery. Such organs include the brain, bladder and uterus.

Although the illustrated embodiments have concentrated on the use of the device to deliver agents to blood-carrying vessels at sites of anastomosis as well as to sites contiguous herewith, the invention is not limited to such uses. The device may, for example, be used more generally to deliver agents to the adventitial surface of non-anastomosed blood-carrying vessels For example, following a balloon angioplasty, a device of the form shown in FIGS. 3 to 5 may be placed around the exterior of an artery in the region of the site of the balloon angioplasty, so as to deliver one or more agents thereto via the adventitial surface of the artery.

In the embodiments described above, the sealed reservoirs are shown as taking the form of a radial space or clearance between the adventitial surface of the blood-carrying vessel and the interior of at least the first body portion, which space is at least part-filled in use by a pharmaceutical formulation. Such a space is not, however, essential. For example, in an alternative embodiment, the body may have a generally impermeable flexible outer layer and a flexible inner layer which is impregnated with the formulation and which is arranged to be in contact the adventitial surface in use.

The outer layer may, for example, be made of solid collagen and the inner layer made of sponge-like collagen cross-linked thereto, the sponge-like layer being capable of being impregnated with the pharmaceutical formulation containing the agent to be delivered. In such a situation, the device may be provided to the surgeon for fitment with the formulation already impregnated therein, or it may be wetted with the formulation after fitment, for example by being injected as described earlier.

Alternatively, the agent may be coated onto an internal surface of the body, which surface is just in contact with the blood vessel in use. Alternatively, agent may be dispersed throughout the structure of the body.

It is desirable that the body of the device should have sufficient strength to resist torsional forces. For this purpose, the body may be formed with, for example, an inner layer, e.g. a collagen film, or longitudinal, transverse or helical ribs. Ribs may be provided that subdivide the reservoir into compartments, and to provide additional stability.

The proteins or nucleic acids may be used for the treatment or prevention of intimal hyperplasia arising from any clinical circumstances. For example, it is possible to treat hyperplasia arising after any type of surgical procedure, including angioplasty, for example balloon angioplasty; bypass surgery, such as coronary bypass surgery in which a vein is anastomosed to an artery; other anastomosis procedures, for example anastomosis in the legs; and endarteriectomy, for example carotid artery endarteriectomy. It is also possible to treat intimal hyperplasia associated with arterial damage or hypertension, for example pulmonary artery hypertension. The invention provides for treatment of intimal hyperplasia in any type of blood vessel, e.g. in an artery or vein, preferably an artery.

According to the invention, it is possible to treat or ameliorate established intimal hyperplasia or to prevent intimal hyperplasia from arising. Similarly, it is possible to diminish the likelihood of intimal hyperplasia arising, or to diminish the severity of established intimal hyperlasia or hyperplasia that is likely to arise. Treatment according to the invention may take place before, during, or after a surgical procedure, for example in order to reduce the chance of hyperplasia arising after the procedure.

Preferably, the VEGF nucleic acid or protein is administered with a view to preventing or treating de novo stenosis. It can, however, also be used to treat or prevent restenosis.

The proteins or nucleic acids of the invention are preferably delivered in the form of a pharmaceutical formulation comprising a pharmaceutically acceptable carrier. Any suitable pharmaceutical formulation may be used.

For example, suitable formulations may include aqueous and non-aqueous sterile injection solutions which may contain anti-oxidants, buffers, bacteriostats, bactericidal antibiotics and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a frozen or freeze-dried (lyophilized) condition requiring only the addition of the sterile liquid carrier, for example water for injection, immediately prior to use.

It should be understood that, in addition to the ingredients particularly mentioned above, formulations of this invention may include other agents conventional in the art having regard to the type of formulation in question. Of the possible formulations, sterile pyrogen-free aqueous and non-aqueous solutions are preferred.

The proteins, nucleic acids and vectors may be delivered in any suitable dosage, and using any suitable dosage regime. Those of skill in the art will appreciate that the dosage amount and regime may be adapted to ensure optimal treatment of the particular condition to be treated, depending on numerous factors. Some such factors may be the age, sex and clinical condition of the subject to be treated.

For the delivery of naked nucleic acids encoding VEGF or constructs comprising such nucleic acids, typical doses are from 0.1-5000 µg, for example 50-2000 µg, such as 50-100 µg, 100-500 µg or 500-2000 µg per dose. For the delivery of VEGF protein, suitable doses include doses of from 1 to 1000 µg for example from 1 to 10 µg, from 10 to 100 µg, from 100 to 500 µg or from 500 to 1000 µg.

The dosage used for the delivery of VEGF nucleic acids by means of viral or non-viral vectors will depend on many factors, including the efficiency with which the vectors deliver VEGF nucleic acids to cells, and the efficiency with which the VEGF nucleic acids are expressed in the cells.

For example, viral vectors may be delivered in doses of from $10^4$ to $10^{14}$ cfu or pfu/ml, for example $10^4$ to $10^6$, $10^6$ to $10^8$, $10^8$ to $10^{10}$, $10^{10}$ to $10^{12}$ or $10^{12}$ to $10^{14}$ cfu or pfu/ml. Doses in the region of $10^5$ to $10^9$ cfu or pfu/ml are preferred. The term pfu (plaque-forming unit) applies to certain viruses, including adenoviruses, and corresponds to the infectivity of a virus solution, and is determined by infection of an appropriate cell culture, and measurement, generally after 48 hours, of the number of plaques of infected cells. The term cfu (colony-forming unit) applies to other viruses, including retroviruses, and is determined by means known in the art generally following 14 days incubation with a selectable marker. The techniques for determining the cfu or pfu titre of a viral solution are well known in the art.

For retroviruses, dosages in the region of $10^5$ to $10^6$ cfu/ml are particularly preferred. For pseudotyped retroviruses, dosages in the region of $10^7$ cfu/ml are particularly preferred. For adenoviruses, dosages in the region of $10^9$ pfu/ml are particularly preferred.

Similarly, such doses may be included within implants of the invention for gradual delivery.

VEGF nucleic acids associated with non-viral vectors may also be delivered in any suitable dosage, by any means of administration, as described above, or gradually from an implant. Suitable doses are typically from 0.1 to 1000 µg of nucleic acid, for example 1 to 100 µg, 100 to 500 µg or 500 to 1000 µg, 1000 to 2000 µg, 2000 to 3000 µg or 3000 to 5000 µg. Preferred doses are in the region of 5 to 50 µg, for example 10 to 20 µg.

Dosage schedules will also vary according to, for example, the route of administration, the species of the recipient and the condition of the recipient. However, single doses and multiple doses spread over periods of days, weeks or months are envisaged. Also, as explained above, the delivery of VEGF proteins and nucleic acids may be effected by means of an implant suitable for fitting around a blood vessel, preferably an artery; preferably, the implant is in the form of a collar. Such an implant will effect gradual delivery. For example, delivery may take place over a period of hours, days, weeks or months.

Proteins and nucleic acids of the invention may be administered by any form of administration, for example topical, cutaneous, parenteral, intramuscular, subcutaneous or transdermal administration, or by direct injection into the bloodstream, direct injection into or around the arterial wall or by direct application to mucosal tissues. Preferably, administration is by means of an implant, as described above.

The proteins, nucleic acids and vectors of the invention may be used to treat intimal hyperplasia in any mammal. Treatment of human patients is preferred.

The invention also provides kits for the treatment or prevention of intimal hyperplasia. These kits comprise (i) as an agent, VEGF protein or nucleic acid, preferably in association with a vector, as defined above; and (ii) an implant of the invention in the form of a collar into which the VEGF protein or nucleic acid may be introduced. Preferably, the VEGF nucleic acid or protein is provided in the form of a pharmaceutical formulation comprising a pharmaceutically-acceptable carrier as defined above. Components (i) and (ii) may be packaged in any suitable way. Other components known in the art may also be included, for example standard reagents and/or solutions and/or equipment.

The invention also provides methods of treating or preventing intimal hyperplasia comprising administering to a patient in need of such treatment an effective non-toxic amount of a VEGF protein, nucleic acid or agonist of the invention. Such treatment is effected in the manner described herein.

The implants of the invention, especially implants in the form of collars, as defined above, can also be used for the delivery of agents other than VEGF to blood vessels, e.g. arteries. Any suitable agent may be delivered in this way, to achieve any desired therapeutic goal.

It has been observed that plasmid/liposome complexes, MMLV retroviruses, VSV-G retroviruses and adenoviruses lead to expression in collared arteries. Gene transfer efficiency was highest with adenoviruses and pseudotyped VSV-G retroviruses also produced a relatively high transfection efficiency. The utility of the replication-deficient VSV-G retroviruses in arterial gene transfer has not been previously demonstrated. Expression was seen in some endothelial cells of the adenovirus-transfected arteries. Since penetration from the adventitia to the intima had occurred, these results raise the general possibility of altering endothelial function in human disease by extralumenal gene transfer using genes other than VEGF. This may also be useful for the expression in the adventitia and outer media of diffusible or secreted gene products which then act elsewhere in the arterial wall. Preferably, such delivery effects treatment of intimal hyperplasia, as defined above, although it may also effect additional or alternative therapeutic goals.

Preferred therapeutic agents for delivery in this manner include proteins other than VEGF that stimulate nitric oxide (NO) production in the arterial wall. The delivery of NO synthases, especially inducible NO synthase (iNOS), to effect treatment or prevention of intimal hyperplasia is particularly preferred.

Other preferred therapeutic agents include agonists which activate the endothelial VEGF receptor (see above). These agonists will typically be small synthetic molecules. Peptides including peptide fragments of VEGF proteins may also be used. In this case, treatment may be effected by delivery of the peptides themselves or of nucleic acids encoding them, as described above for VEGF. These are preferably delivered by the same route, i.e. via an implant as defined herein, though they could be delivered systemically.

Preferably, the therapeutic agents will be in the form of nucleic acid encoding a pharmaceutically-active polypeptide or protein. More preferably, this nucleic acid will be comprised within a construct, as defined above. Still more preferably, the nucleic acid or construct will be delivered to the artery by means of a vector as defined above, for example a viral or non-viral vector as defined above.

Thus, extra-arterial gene transfer can be used for the delivery of genetic material into the wall of blood vessels, preferably arteries. From the Examples, it can be seen that changes in medial SMC and even endothelium change can be achieved from the adventitial side, allowing the development of new methods for the treatment of blood vessel, e.g. arterial, disease.

Accordingly, the invention provides the use, in the manufacture of a medicament for the treatment or prevention of intimal hyperplasia of a blood vessel, of NOS (optionally iNOS), or a nucleic acid encoding NOS (optionally iNOS); wherein the NOS protein or nucleic acid is provided in an implant, preferably a collar, as defined above for VEGF.

The invention also provides kits comprising (i) NOS (optionally iNOS) protein or nucleic acid; and (ii) an implant of the invention. These kits are as described above for VEGF. These are suitable for the treatment or prevention of intimal hyperplasia of a blood vessel.

The invention also provides a method of treating intimal hyperplasia of a blood vessel comprising implanting an implant of the invention comprising NOS protein or nucleic acid in the vicinity of the hyperplasia to be treated or prevented, thereby to effect delivery of NOS protein or nucleic acid.

NOS nucleic acid is preferably associated with a vector, as described above for VEGF. Treatment is carried out as described above for VEGF, and dosages and pharmaceutical formulations are also as described above for VEGF.

The invention also provides implants of the invention which comprise NOS (optionally iNOS), protein or nucleic acid.

The finding that VEGF stimulates NO and prostacyclin production in the arterial wall also suggests that VEGF and agonists of VEGF receptors will be useful in the treatment of other NO-linked and/or prostacyclin-linked conditions.

In particular, VEGF and agonists of the receptors to which VEGF binds may be used to treat hypertension, or high blood pressure. Forte et al, Lancet (1997) 349:837-42, found that low NO levels are characteristic of individuals suffering from essential (i.e. systemic) hypertension. NO is known to relax the walls of blood vessels; Forte et al suggest that impaired NO production reduces this relaxation, leading to constriction of blood vessels and so to increased blood pressure. Further, in individuals suffering from essential hypertension, levels of prostacyclin may be depressed.

Since VEGF stimulates NO and prostacyclin production, it may be useful in combating high blood pressure. More specifically, an agent of the invention may be useful in therapy of three diseases of particular interest.

The first is essential hypertension, i.e. systemic high blood pressure at any location, or all around the body. For the treatment of essential hypertension, which is a systemic condition, it is preferred that a VEGF protein or agonist of the invention be delivered in a systemic manner, e.g. by systemic delivery of VEGF nucleic acids encoding VEGF proteins or agonists, by gene therapy.

The second is cor pulmonale, i.e. right heart failure caused by high blood pressure in the pulmonary artery. This may be treatable by administering VEGF nucleic acids, proteins and agonists as described herein, especially by delivering VEGF DNA to the artery via an arterial collar (see above) with subsequent expression of the DNA to yield protein in the arterial wall.

The third is primary pulmonary hypertension, i.e. high blood pressure in the lungs. This usually leads, ultimately, to heart failure and death, and is currently only treatable by means of continuous prostacyclin infusion or a lung transplant. Here, the preferred treatment technique would be to transform or transfect lung tissue with a nucleic acid encoding VEGF or an agonist thereof, thereby generating VEGF in vivo and stimulating NO and/or prostacyclin production.

Accordingly, the invention provides the use of an agent selected from Vascular Endothelial Growth Factor (VEGF), a nucleic acid encoding VEGF, an agonist of VEGF, and a nucleic acid molecule encoding an agonist of a receptor to which VEGF binds, in the manufacture of a medicament for the stimulation of nitric oxide (NO) or prostacyclin production in vivo.

Kits of the invention which comprise VEGF proteins, or nucleic acids, or agonists of a receptor to which VEGF binds or nucleic acids encoding such agonists are also suitable for the treatment of hypertension.

The invention also provides a method of treating or preventing hypertension comprising administering to a patient an effective non-toxic amount of a VEGF protein, nucleic acid or agonist of the invention. Such treatment is effected as described herein. For primary pulmonary hypertension, the preferred method is transformation of lung tissue with a VEGF-encoding nucleic acid or a nucleic acid encoding an agonist of a receptor to which VEGF binds, as defined herein.

A further condition that can be treated according to the invention is atherosclerosis, which may be an NO-linked and/or prostacyclin-linked condition. Where the treatment of atherosclerosis is concerned, it is preferred to use a VEGF agonist as defined herein.

Thus, the invention provides the use of an agent selected from Vascular Endothelial Growth Factor (VEGF), a nucleic acid encoding VEGF, an agonist of VEGF, and a nucleic acid molecule encoding an agonist of a receptor to which VEGF binds, in the manufacture of a medicament for the treatment of atherosclerosis by stimulation of NO and/or prostacyclin production in vivo.

The invention also provides a method of treating or preventing atherosclerosis comprising administering to a patient an effective non-toxic amount of a VEGF protein, nucleic acid or agonist of the invention. Such treatment is effected as described herein.

For treatment of atherosclerosis, one preferred mode of delivery is oral delivery, e.g. in tablet form, of a VEGF protein of the invention or, preferably, of a VEGF agonist of the invention.

The following Examples illustrate the invention. The following abbreviations are used:
BSA—bovine serum albumin
DMEM—Dulbecco's modified Eagle's medium
FCS—Fetal calf serum
HUVEC—Human umbilical vein endothelial cells
IgG—Immunoglobulin G
MAP kinase—mitogen-activated protein kinase
mAb—monoclonal antibody
PBS—phosphate buffered saline
$PGI_2$—prostacyclin
$cPLA_2$—cytosolic phospholipase $A_2$
PlGF—placenta growth factor
SDS PAGE—sodium dodecyl sulphate—polyacrylamide gel electrophoresis
VEGF—vascular endothelial growth factor
vWF—von Willebrand's factor
VSMC—vascular smooth muscle cells

EXAMPLE 1

The effect of endothelial cell (EC)-specific VEGF gene transfer on the thickening of the intima was studied using a silicone collar inserted around carotid arteries which acted both as the agent that caused intimal smooth muscle cell growth and as a reservoir for the gene and vector. The model preserved EC integrity and permitted direct extravascular gene transfer without any intravascular manipulation.

EXAMPLE 1.1

Gene Transfer: Intimal thickening was induced in the carotid arteries of thirty-two New Zealand White rabbits by inserting an inert silicone collar around the arteries under a general anaesthesia (Booth et al, Atherosclerosis (1989) 76:257-268). Gene transfer was done five days after positioning of the collar by gently opening the collar under anaesthesia and injecting 500 pi plasmid/liposome complexes into the collar (i.e. on the adventitial surface of the artery). No intravascular manipulations were involved in any steps of the studies.

Plasmid/liposome Complexes: Twenty-five µg pCMV5-VEGF-164 plasmid (containing mouse VEGF cDNA (Breier et al, Development (1992) 114:521-32; nucleotides 1-583) was complexed with 25 µl Lipofectin (BRL) while diluted to 500 µl with Ringer solution. Complexes were kept at room temperature at least 15 min before the gene transfer. It was determined previously that at the concentration used in the present study plasmid/Lipofectin complexes were not toxic to rabbit aortic EC in vitro. Control arteries were transfected with a similar plasmid/liposome complex containing *E. coli* lacZ cDNA (Kalnins et al, supra) (nucleotides 1-3100)

expression plasmid. Plasmids used for the studies were isolated from *E. coli* cultures (DH5α) using Qiagen Mega columns and purified using three phenol/chloroform extractions and one ethanol precipitation (Ausubel et al, eds. Current Protocols in Molecular Biology. New York, N.Y.: Greene Publishing Associates and John Wiley & Sons (1991) 4.2.3-4.2.4) were adjusted to 1 µg/µl and analysed to be free of any microbiological or endotoxin contamination (Limulus assay, detection limit 0.2 ng). Animals were sacrificed 3 (n=8), 7 (n=12) and 14 (n=12) days after the gene transfer operation; arteries were carefully removed and divided into three equal portions: the proximal third was immersion-fixed in 4% paraformaldehyde/PBS for 15 min and embedded in OCT compound (Miles Scientific) (Ylä-Herttuala et al: J. Clin. Invest. (1995) 95: 2692-2698). The middle third was fixed as above for 4 h, rinsed in 15% sucrose for 48 h and embedded in paraffin. The distal third was directly embedded in OCT compound and frozen in liquid nitrogen. In four arteries, the distal third was used for mRNA isolation and RT-PCR (see below). Ten randomly selected sections from the middle portion were used for the determination of intima/media thickness ratio (Ylä-Herttuala et al: Arteriosclerosis (1986) 6; 230-236) by two independent observers without knowledge of the origin of the samples. Mean values of the two independent measurements were used to calculate the results (mean±SD). Differences in the intima/media thickness ratios between the groups were analysed by ANOVA, followed by modified t-test ($*p<0.05$).

RT-PCR: Distal portions of VEGF (n=2) and lacZ (n=2) transfected arteries collected 7 days after the gene transfer were used for mRNA isolation (Micro-FastTrack, Invitrogen) and were reverse-transcribed to the first strand cDNA using AMLV reverse transcriptase (5U per reaction, Boehringer) using random hexamer primers (cDNA cycle Kit, Invitrogen) as described (Hiltunen et al: Circulation (1995) 92:3297-3303). A thirty-five cycle PCR was performed with Taq polymerase (Boehringer) and primers specific for the transfected pCMV5-VEGF-164 construct (5'-primer: SEQ ID No. 9; 3'-primer: SEQ ID. No. 10; PCR cycle parameters: 1 min 90° C., 1 min 60° C., 1 min 72° C., except for the last cycle 5 min).Amplified fragment with an expected length (547 nt) was seen in the VEGF-transfected arteries. DNA size markers (1 kb ladder, BRL) are shown on both sides of the gel.

Micrographs were taken, showing the characteristics of rabbit carotid arteries 7d after VEGF or lacZ gene transfer. Immunostainings of the transfected arteries demonstrated: Control artery transfected with lacZ-plasmid/liposomes (SMC-specific MAb HHF-35, 1:500 dilution, Enzo Diagnostics) showed typical intimal thickening; Artery transfected with VEGF plasmid/liposomes (SMC-specific MAb HHF-35) showed only limited intimal thickening; Endothelium was present in all studied vascular segments (serial section to A, EC-specific MAb CD31, dilution 1:50, DAKO); No evidence of inflammation was detected in VEGF- and lacZ-transfected arteries (Macrophage-specific MAb RAM-11 dilution 1:500, DKO); Neovascularization in the adventitia of VEGF-transfected artery was seen 14 days after gene transfer (Hematoxylin-eosin staining).

The avidin-biotin horseradish peroxidase system (Vector Elite, Vector Labs) was used for the immunostainings (Ylä-Herttuala et al, PNAS (1990) 87: 6959-6963). Controls for the immunostainings included incubations with irrelevant class- and species-matched immunoglobulins and incubations where the primary antibodies were omitted. In situ hybridizations were done using an anti-sense VEGF riboprobe (583 nt) synthesized from pBluescript SK plasmid (Stratagene) as described (Ylä-Herttuala et al (1990), supra). Briefly, paraffin-embedded sections were pretreated with Proteinase K, acetylated and hybridized using 35-S-UTP (DuPont, NEN)-labelled riboprobes ($6\times10^6$ cpm/ml) at 52° C. for 16 h. Final wash after the hybridization was with 0.1×SSC at 60° C. for 30 min. Autoradiography was used for the signal detection (Eastman-Kodak NAB-2). Control hybridizations with a nonhybridizing sense riboprobe (Ylä-Herttuala et al (1990), supra) gave negative results. Sections were counter stained with hematoxylin.

EXAMPLE 1.2

Gene transfer was carried out as described in Example 1.1. L-NAME (70 mg/kg/d) was given to the rabbits in drinking water, starting one day before VEGF (n=5) or lacZ (n=5) gene transfer. Animals were sacrificed 7 days after gene transfer and analysed for the intima/media thickness ratio and histology as described above (Ylä-Herttuala et al, Arteriosclerosis (1986) 6: 230-236; Ylä-Herttuala et al (1990) supra). The difference in intimal thickening was abolished.

EXAMPLE 1.3

Confluent cultures of HUVEC were washed twice with serum-free medium and incubated with this medium either in the presence of the concentrations of recombinant human VEGF indicated for 15 min, or with 10 ng/ml VEGF for the times shown. In some experiments, cells were pretreated for 1 h with 100 µM L-NAME and subsequently treated either with or without. 10 ng/ml VEGF for 10 min. The medium was removed and cells were rapidly lysed at 4° C. by addition of 10 mM Tris/HCl (pH 7.6), 5 mM EDTA, 50 mM NaCl, 30 mM sodium pyrophosphate, 50 mM NaF, 0.1 mM $Na_3VO_4$, 1 mM PMSF and 1% Triton X-100 (lysis buffer). Lysates were clarified by centrifugation at 15000×g for 10 min, and immunoprecipitations were performed by incubating clarified lysates with PY20 anti-phosphotyrosine mAb for 2 h at 40° C. Immunoprecipitates were collected by incubating lysates for a further 1 hour with protein A-agarose. Immunoprecipitates were washed three times with lysis buffer and proteins were then extracted with 2×SDS-PAGE sample buffer. After SDS-PAGE, immunoprecipitated proteins were transferred to membranes and then immunoblotted with PY20 mAb. This shows that VEGF induces phosphorylation of a major 205 kD protein corresponding to VEGF receptor (the major tyrosine phosphorylated proteins at 100, 125, 145, 190 and 205). L-NAME abolishes the response to VEGF.

Recombinant VEGF was added at the concentration of 25 ng/ml for times up to 2 h (nitrite production was increased from the intimal level of c. 16 µM, and remained at 1.8-2 µM). or at the indicated concentrations of 0, 2.5, 25 ng/ml for 10 minutes. Effect of L-NAME (100 µM) pretreatment (1 hour) on the VEGF response was measured after addition of 25 ng/ml VEGF for 10 minutes. Nitrite production was measured using capillary detection method (Leone et al, in Methods in Nitric Oxide Research, Feelisch and Stanler, eds. John Wiley & Sons, New York (1996) 499-508). The level rose to c. 19 and c. 2.1 µM in the presence of VEGF; it was reduced to the control level (c. 17 µM) on the addition of L-NAME.

Results: It was found that, as compared with lacZ-transduced arteries, VEGF gene transfer significantly reduced intimal thickening one week after the operation (intima/media ratio 0.3 vs 1.1, <0.05, respectively). The effect was reduced after two weeks, which is probably due to the fact that the plasmid/liposome-mediated gene transfer typically only induces temporary expression of the transfected gene with maximal protein expression between 2-3 days after the gene transfer (Nabel et al, Ann. Rev. Physiol. (1994) 56: 741-761).

Immunohistochemical analysis of the arteries showed that intimal thickening was almost exclusively composed of SMC. Endothelial layer was present in all studied segments. No adverse effects or inflammation were detected in the transfected arteries.

Expression of the transfected VEGF was confirmed by RT-PCR using primers specific for the transgene and by in situ hybridization. Most of the VEGF and lacZ expression occurred in the adventitia and outer media in fibroblasts and SMCs. Adventitial neovascularization was seen in three of the VEGF-transfected arteries 14 days after the gene transfer. No neovascularization was detected in lacZ-transfected arteries.

It has been shown previously that lacZ-plasmid/liposome gene transfer using the collar model leads to a local gene transfer in 0.05% of arterial cells. In spite of the low gene transfer efficiency, the secreted form of VEGF produced inside the collar leads to biological effects in the local arterial microenvironment, as indicated by the presence of neovascularization in three VEGF-transfected arteries 14 days after gene transfer. As in acute hypoxia, secreted VEGF is believed to reach the EC by diffusion and bind to VEGF receptors on EC.

It was hypothesized that the inhibitory effects of VEGF on intimal thickening were due to either a direct or indirect VEGF-induced EC-derived factor or activity that could, in turn, inhibit SMC proliferation. In particular, it was hypothesized that the effects of VEGF on intimal thickening were mediated through the NO pathway. This hypothesis was tested in a subset of New Zealand White rabbits (n=8) by giving the animals NO synthase inhibitor L-NAME during the gene transfer experiments. It was found that L-NAME abolished the difference in intimal thickening between VEGF- and lacZ-transfected arteries. The main target cells for VEGF in the arterial wall are EC. The only other cell types possessing VEGF receptors are monocytes but, as judged from immunocytochemistry with specific antibodies, monocytes are absent from the collared carotid arteries under these conditions.

These results (the abilities of difference in intimal thickening) were consistent with VEGF-induced inhibition of intimal thickening through the stimulation of NO production. It was therefore examined whether VEGF could directly stimulate NO production in cultures of EC. VEGF induced tyrosine phosphorylation of a major 205 kDa protein corresponding to the VEGF receptor within the concentration range 1-25 ng/ml. Addition of VEGF to cultured human umbilical vein endothelial cells (HUVEC) caused a time- and concentration-dependent increase in NO production as monitored by measurement of nitrite levels. The effect of VEGF on NO production was seen as early as 30 seconds after the addition of VEGF, reached a maximum after 5 min and was sustained for up to 2 hours. The half-maximal effect of VEGF was obtained at 5 ng/ml. VEGF-induced phosphorylation and NO production were completely abolished in the presence of 100 µM L-NAME. Thus, it is likely that VEGF gene transfer stimulates NO production in EC in the transfected arteries and limits SMC proliferation at least partially via an NO-mediated mechanism. The findings are compatible with the previous observations that transfection of arteries with endothelial NO synthase cDNA reduces intimal thickening (Von der Leyon et al, PNAS (1995) 92:1137-1141).

Callow et al (supra) and Asahara et al (supra) concluded that administration of VEGF protein stimulated EC proliferation in denuded arteries, but the actual mechanisms involved in the inhibition of intimal thickening were not studied. In the collared carotid artery, intimal thickening is stimulated in the presence of an anatomically intact endothelium. Therefore, it is unlikely that the inhibitory effect of arterial VEGF gene transfer on intimal thickening reported here is due to VEGF-stimulated re-endothelialization. According to these results, VEGF can directly induce NO production in HUVEC such that this is one mechanism through which VEGF can inhibit intimal thickening. VEGF may also stimulate the production of other factors which can negatively regulate SMC proliferation including TGF-β or prostacyclin.

EXAMPLE 2

Using plasmid/liposome complexes for gene delivery, Moloney murine leukemia virus-derived (MMLV) retroviruses, pseudotyped vesicular stomatitis virus protein-G (VSV-G)-containing retroviruses and adenoviruses were delivered into the rabbit carotid artery using a silastic collar applied to the adventitia. The collar is used because 1) it provides a gene delivery reservoir; 2) no intralumenal manipulations are performed and endothelium remains anatomically intact throughout; and 3) installation of the collar induces arterial smooth muscle cell (SMC) proliferation and enhances retroviral gene transfer efficiency where target cell proliferation is required.

Gene Transfer: New Zealand White rabbits (1.8-2.5 kg) were used. The anaesthetic was fentanyl-fluanisone (0.3 ml/kg)/midazolam (1 mg/kg) (Ylä-Herttuala et al, J. Clin Invest. (1995) 95:2692-2698). A midline neck incision exposed the left carotid artery. A biologically inert 2 cm silastic collar (MediGene Oy, Kuopio, Finland) was positioned around the carotid artery so that it touched the adventitia lightly at either end (Booth et al, supra). Gene transfer was performed 4-5 days after the collaring operation. For gene transfer, animals were re-anaesthetized. The collar, which had been surgically re-exposed, was gently opened and filled with 500 µl of the gene transfer solution (see below). The incision was closed and arteries later analysed for gene transfer efficiency.

Histological Analysis: Collared arteries were carefully removed and divided into three equal parts: the proximal third was immersion-fixed in 4% paraformaldehyde/PBS (pH 7.4) for 15 min followed by embedding into OCT compound (Miles Scientific, USA). The medial third was immersion-fixed in 4% paraformaldehyde/PBS (pH 7.4) for 4 h, rinsed in 15% sucrose (pH 7.4) for 48 h and embedded in paraffin. The distal third was embedded in OCT compound and processed for frozen sections. Ten randomly selected sections were stained with X-gal for β-galactosidase activity for 12 h and used for the determination of gene transfer efficiency (Nabel et al, Science (1990) 249: 1285-1288, Ylä-Herttuala et al, (1995) supra). Gene transfer efficiency was calculated as a percentage of the β-galactosidase-containing cells as a proportion of the total number of nuclei in 20 randomly selected 100× fields. Randomly selected sections from each third portion of the collared arteries were used for immunocytochemistry and analysis of cell types and/or intima/media thickness ratios (Booth et al, supra).

Cell types were identified using the following antibodies: SMC: HHF-35 mAb (1:500 dilution, Enzo Diagnostics, USA), α-actin mAb (1:1000 dilution; Sigma Chemical Co.); macrophages: RAM-11 mAB (1:1000 dilution; Dako, USA), anti-CD68 mAb (1:250 dilution; Dako); endothelial cells: anti-CD31 mAb (1:50 dilution; Dako); polymorphonuclear leukocytes: anti-CD45 mAb (1:100 dilution; Dako); and anti-rabbit T-cells: MCA 805 mAb (1:1000 dilution; Dako). The avidin-biotin-horseradish peroxidase system was used for signal detection (Vector laboratories) (Ylä-Herttuala et al (1995) supra). After immunostaining, tissue sections were counter-stained with hematoxylin. Determination of the Proliferation Index: The proliferation index in the collared arteries was determined using the 5-bromo-2'-deoxyuridine (BrdU) labelling (Soma et al, Arterioscler. Thromb. (1993) 13:571-578). Briefly, New Zealand white rabbits (n=12) were injected with BrdU (40 mg/kg body weight) 3 h before sacrifice. Carotid arteries were fixed in 70% ethanol overnight and embedded in paraffin. Serial sections (20 sections per animal) were stained to detect BrdU using FITC-labelled anti-mouse IgG (Dako), following propidium iodide staining of the nuclei. The labelling index was calculated as the percentage of the BrdU-positive nuclei. Contralateral carotid arteries were sham-operated and used as controls.

Plasmid/liposomes: pCMV-β-galactosidase (lacZ) expression plasmid (Promega) was complexed with Lipofectin reagent (BRL) as follows: 25 µg plasmid was slowly mixed with 25 µl Lipofectin reagent while diluted to 500 µl with Ringer solution. No precipitates were observed in the plasmid/Lipofectin solution. The mixture was left to stand at room temperature for at least 15 min and used for gene transfer within two hours. Plasmid preparations were checked for the absence of lipopolysaccharide contamination (Limulus assay, Sigma Chemical Co.).

Retroviruses: LacZ-containing pLZRNL MMLV retroviruses (Ylä-Herttuala et al, (1995) supra; Miyanohara et al, PNAS (1988) 85:6538-6542) or LacZ VSV-G pseudotyped retroviruses (Yee et al, PNAS (1994) 91:9564-9568) were used for the studies. In both, the expression of lacZ is driven by the 5' LTR. Replication-deficient LZRNL amphotrophic retroviruses were packaged in PA317 cells and used at a titer of $5 \times 10^5$ cfu/ml as described (Ylä-Herttuala et al, (1995) supra). Replication-deficient VSV-G pseudotyped retroviruses were produced in 293 GP cells using transient transfection (Yee et al, supra). Pseudotyped retroviruses were concentrated using ultracentrifugation and used at a titer of $1 \times 10^7$ cfu/ml. Before use, retroviral preparations were checked for the absence of any bacteriological contaminants or helper viruses (Yee et al, supra).

Adenoviral Vectors: Replication-deficient E1-deleted adenoviruses were used for the studies (Gosh-Choudhury et al, Gene (1986) 50: 161-171; Simari et al, J. Clin. Invest. (1996) 98: 225-235). Nuclear-targeted β-galactosidase cDNA under a β-actin-promoter and a CMV enhancer was cloned into the E1-deleted region of the adenoviral genome using homologous recombination (Gosh-Choudhury et al, supra; Simari et al, supra). Replication-deficient adenoviruses were produced in 293 cells and concentrated by ultracentrifugation. Titers of $1 \times 10^9$ pfu/ml were used for the gene transfer experiments. Adenoviral preparations were analysed for the absence of helper viruses or bacteriological contaminants (Gosh-Choudhury et al, supra).

Results: The adventitial collar led to neointimal hyperplasia 7-14 days after the operation. The endothelium remained anatomically intact throughout the studies. BrdU labelling indicated a peak proliferation index of 23% 3 days after the operation. The neointima was exclusively composed of SMC. Plasmid/liposome complexes led to a detectable gene transfer into the adventitia and outer media, with an efficiency of less than 0.01%. Untransfected or liposome-treated collared arteries showed no staining for β-galactosidase activity.

Adventitial retroviral gene transfer was less efficient without the collar, probably because retroviral gene transfer only occurs in proliferating cells. The gene transfer efficiency with replication-deficient MMLV retroviruses was low (less than 0.01%). Gene transfer efficiency with VSV-G pseudotyped retroviruses was 0.1%. Using MMLV and VSV-G retroviruses, β-galactosidase staining was observed in the adventitia and outer media.

Replication-deficient adenoviruses gave efficient gene transfer, β-galactosidase staining being detected in the adventitia and outer media. Interestingly, staining was also observed in some endothelial cells and in some intimal cells. Since the lacZ adenovirus construct contained a nuclear localization signal for β-galactosidae, intense X-gal staining was located in the nuclei of the transfected cells. Gene transfer efficiency was approximately 10%, as estimated from the total number of stained nuclei in the analysed sections. Some inflammatory cells were seen in VSV-G retrovirus and adenovirus-transfected arteries. No inflammatory cells were seen in the plasmid/liposome transfected arteries.

In this Example, the transfer of the β-galactosidase (lacZ) marker gene to the adventitia and outer media occurred with all gene transfer systems. Adenoviruses also transferred the β-galactosidase gene to some endothelial cells. After five days, adenoviral vectors produced the highest gene transfer efficiency, with up to 10% of cell showing β-galactosidase activity. Pseudotyped VSV-G retroviruses were also effective in achieving gene transfer in 0.1% of cells in the adventitia and outer media. Plasmid/liposome complexes and MMLV retroviruses infected <0.01% of cells. No adverse tissue reactions were observed with any of the gene transfer systems.

Thus, replication-deficient adenoviruses, VSV-G pseudotyped retroviruses and plasmid/liposome complexes can be used for gene transfer to the arterial wall using the collar method. Effects on medial SMC and even endothelium can be achieved from the adventitial side.

EXAMPLE 3

In this Example, the stimulation of $PGI_2$ by VEGF was examined.

Cell Culture: HUVECs were obtained either from Clonetics and cultured in the manufacturer's own medium supplemented with 2% FBS, or were grown from fresh umbilical cords by collagenase digestion and cultured on 1% gelatin-coated plates in medium 199 supplemented with 20% FCS and endothelial cell growth supplement (Wheeler-Jones et al, Biochem. J. (1996) 315:407-416). For experimental purposes, primary cultures of HUVEC were dispersed by treatment with 0.05% trypsin/0.02% EDTA for 5 min at 37° C. and then replated in either 90 mm, 60 mm or 35 mm plastic dishes, or onto 24-well plates. Cultures were maintained in a humidified atmosphere containing 5% $CO_2$ and 90% air at 37° C. and used after 6-8 days or when the cells had formed a confluent monolayer.

PGI$_2$ Assay: Confluent cultures of HUVEC in 24-well plates were washed twice in serum-free M199 (pH 7.4) and exposed to medium containing VEGF. The PGI$_2$ content of cell supernatants was quantified by radioimmunoassay of 6-keto-PGF$_{1\alpha}$, the stable breakdown product of PGI$_2$ as previously described (Wheeler-Jones et al, supra).

Arachidonic Acid Release: Arachidonic acid release was determined essentially as described (Domin and Rozengurt, J. Biol. Chem. (1993) 268:8927-8934.). Confluent HUVEC cultures were incubated for 24 h with [5,6,8,9,11,12,14,15-$^3$H]arachidonic acid (1 mCi/ml, 211 Ci/mmol). The cells were then washed twice with medium 199 and incubated in 1 ml of this medium supplemented with 0.3% BSA (essential fatty-acid free) and VEGF or thrombin. After treatment, the medium was removed, centrifuged in a microcentrifuge at 16,000×g for 5 min, and the radioactivity in the supernatant was determined by counting in a scintillation counter.

Western Blotting Procedures: Treatment of quiescent cultures of cells with factors, and cell lysis were performed as described above and in the Results and Figure Legends. After SDS-PAGE, proteins were transferred to Immobilon membranes (Millipore Inc.). For MAP kinase assays, membranes were blocked using 5% non-fat dried milk in PBS, pH 7.2, and incubated for 3-5 h in PBS/0.05% Tween-20 containing primary antibody (1 mg/ml) as indicated. For immunoblots with antibody to cPLA$_2$, membranes were blocked for 3 h in TBST50 mM Tris/HCl, 150 mM NaCl, 0.02% (v/v) Tween 20 pH 7.4 (TBST) containing 0.2% (w/v) 1-block (Tropix), then incubated with primary antiserum in TBST. Membranes were then washed six times (10 min each wash) in TBST and incubated for 1 hour in TBST containing HRP-conjugated secondary antibody. Immunoreactive bands were visualized by chemiluminescence using HRP-conjugated anti-mouse or anti-rabbit IgG and ECL™ reagent according to the manufacturers instructions.

MAP Kinase Assay: Cells were treated with factors as indicated, washed rapidly twice with ice-cold PBS and immediately extracted by the addition of 100 ml boiling 2×SDS-PAGE sample buffer. Cell extracts were collected by scraping, heated to 95° C. for 10 min and run on 12.5% acrylamide SDS-PAGE gels. Following transfer to Immobilon membranes, proteins were immunoblotted with an antibody which specifically recognizes p42 and p44 MAP kinases (Erk-1 and Erk-2) activated by phosphorylation at Tyr204 (Payne e al, EMBO J. (1991) 10:885-892.).

cPLA$_2$ Mobility Shift Assay: Confluent quiescent HUVECs in 60 mm dishes were washed twice in serum-free medium 199 (pH 7.4) and subsequently exposed, for the times indicated, to medium containing factors as detailed in the Figure legends. Cell lysates were prepared as previously described (Wheeler-Jones et al, supra). Proteins were separated by SDS-PAGE (10% acrylamide) and after transfer to membranes were immunoblotted with polyclonal anti-serum to cPLA$_2$ (BorschHaubold et al, J. Biol. Chem. (1995) 270: 25885-25892; and Kramer et al, J. Biol. Chem. (1996) 271:27723-27729).

Assay of vWF Secretion: vWF secretion was measured by ELISA (Wheeler-Jones et al, supra) in samples of medium obtained from confluent cultures of HUVECs which had been treated with factors, as indicated. Plates were coated with the anti-vWF mAb CLBRAg35, and the lower detection limit of the assay was approximately 1.0 mU/ml.

Materials: Recombinant VEGF was obtained either from UBI or from R & D Systems. Recombinant PIGF was the gift of Professor Werner Risau and was also obtained from R & D Systems. Polyclonal cPLA2 antiserum was kindly provided by Dr. Ruth Kramer (Eli Lilly, Indianapolis). The anti-vWF mAb CLBRAg35 was a gift from Dr. J. A. Van Mourik (Central Blood Laboratory, Amsterdam, The Netherlands). Antibody to the activated phosphorylated form of p42/p44 MAP kinase was purchased from New England Biolabs Inc. [5,6,8,9,11,12,14,15-$^3$H]arachidonic acid, ECL™ reagents and HRP-conjugated anti-mouse IgG were from Amersham, UK. Goat anti-rabbit HRP-conjugated IgG was obtained from Pierce Inc. All other reagents used were of the purest grade available.

Results: Confluent cultures of HUVEC were treated for various times up to 2 h with VEGF and the medium was removed at these times and assayed for the presence of 6-keto PGF$_{1\alpha}$, a stable metabolic breakdown product of PGI$_2$. VEGF caused a time-dependent increase in the production of PGI$_2$ which was detectable as early as 15 min after addition of the factor, continued to increase for up to 60 min, and was sustained thereafter for up to 2 h. Control cells exhibited only a small increase in PGI$_2$ production during the time-course examined. VEGF stimulation of PGI$_2$ production was also concentration-dependent. After a 60 min incubation, an increase in PGI$_2$ synthesis was detectable at 5 ng/ml, was half-maximal at 10 ng/ml and reached a maximum at 15 ng/ml. It was consistently noted that VEGF-induced PGI$_2$ synthesis underwent a small decline at 25 ng/ml.

It was also examined whether the VEGF-related factor PIGF, a specific ligand for the Flt-1 VEGF receptor, could elicit PGI$_2$ synthesis in HUVEC. In 5 independent experiments, the PIGF stimulated PGI$_2$ synthesis significantly more weakly than VEGF. The responses of both VEGF and PIGF were also compared to that of thrombin, a potent inducer of prostanoid synthesis in endothelial cells and platelets. In several independent experiments in which the effects of VEGF, PIGF and thrombin were directly compared in parallel cultures, the mean fold increases in 6-keto PGF$_{1\alpha}$, produced by 60 min incubations with 25 ng/ml VEGF, 60 ng/ml PIGF and 1 U/ml thrombin were, respectively, 2.0-, 1.3- and 4.4-fold above the mean control unstimulated level.

If VEGF stimulation of PGI$_2$ synthesis was mediated through activation of an isoform of PLA$_2$, it would be predicted that VEGF would cause a rapid mobilization of arachidonic acid from cells. To test this, HUVECs were preincubated with radio-labelled arachidonic acid for 24 h and subsequently challenged with VEGF for different times. VEGF caused an increase in label released into the medium of prelabelled cells which was evident 10 min and reached a maximum 30 min, after addition of the factor. As measured in parallel cultures, the time-course for VEGF-stimulated arachidonic acid release was very similar to that for thrombin. The concentration-dependence for VEGF-stimulated arachidonic acid release was very similar to that obtained for PGI$_2$ production, with a half-maximum effect at 2.5-5 ng/ml and a maximum at 10-20 ng/ml. Similarly to the relative abilities of thrombin and VEGF to stimulate PGI$_2$ production, maximum VEGF-induced arachidonic acid release was consistently lower than that obtained for thrombin. In four independent experiments, VEGF and thrombin caused mean increases in the release of labelled arachidonic acid of 1.6- and 3.4-fold above the basal unstimulated level, respectively. PIGF caused no detectable significant increase in arachidonic acid release from prelabelled HUVECs.

One plausible mechanism for rapid VEGF-stimulated arachidonic acid release is the direct enzymatic release of arachidonic acid catalysed by the cytosolic form of $PLA_2$. $cPLA_2$ can be activated by MAP kinase-dependent phosphorylation and, similarly to the phosphorylation and activation of other enzymes including MAP kinases, the conversion of $cPLA_2$ to its activated form can be monitored by a shift in its mobility in SDS-PAGE gels from a fast- to a slow-migrating form. Accordingly, activation of $cPLA_2$ in response to VEGF was determined by western blot analysis of HUVEC extracts using a specific antibody to $cPLA_2$ (BorschHaubold et al, supra, and Kramer et al, supra). In extracts of control unstimulated HUVECs, antibody to $cPLA_2$ recognized two distinct bands of approximately equal intensity and migrating with approximate Mr 97,000. Although $cPLA_2$ has a predicted molecular weight of 85 kDa, this protein has previously been reported to migrate in SDS-PAGE as a 97 kDa band (BorschHaubold et al, supra, and Kramer et al, supra).

VEGF at 25 ng/ml caused a marked increase in the immunoreactivity of the slow-migrating form of $cPLA_2$ and a concomitant relative decrease in the faster-migrating form, which was detectable after 2 min, reached a maximum after 15 min, and was sustained for up to 60 min after VEGF addition. In five independent experiments, VEGF consistently caused a marked increase in the immunoreactivity of the slower-migrating form of $cPLA_2$. The VEGF-induced decrease in the electrophoretic mobility of $cPLA_2$ was also concentration-dependent, with a noticeable increase in the slow-migrating form at 2.5 ng/ml and a maximum increase at 5-10 ng/ml, the highest concentration tested. While VEGF caused an apparent reduction in the level of the faster-migrating form of $cPLA_2$, this species was evident at all VEGF concentrations and times of treatment examined. Thrombin also caused a striking shift in the mobility of $cPLA_2$ from a faster- to a slower-migrating form, both of which exactly co-migrated with those detected in extracts of VEGF-treated HUVECs. Direct comparison of the effects of VEGF and thrombin in the same experiment showed that, similarly to the results obtained for $PGI_2$ synthesis and arachidonic acid release, thrombin caused a more marked increase in the gel retardation of $cPLA_2$ with virtually complete disappearance of the faster-migrating form of the enzyme. PlGF caused no detectable shift in the mobility of immunoreactive $cPLA_2$ from faster to slower-migrating forms.

It was further examined whether VEGF also induced vWF secretion by HUVECs. VEGF stimulated a time- and concentration-dependent production of vWF. vWF was detectable in HUVEC medium as early as 30 min after addition of 25 ng/ml VEGF to cells and continued to increase over the time-course examined reaching a level 2.5-fold above that in control cells after 3 h. The concentration-dependence for the effect of VEGF was similar to that obtained for $PGI_2$ production with a half-maximal response at approximately 10 ng/ml and a maximum effect at 25 ng/ml, the highest concentration tested. Similarly to the results obtained for $PGI_2$ synthesis, the effect of VEGF was comparable to, though consistently weaker than, that of thrombin (FIG. 12A). In contrast VEGF, PlGF caused no detectable stimulation of vWF secretion in HUVEC. Comparison of the effects of VEGF and PlGF on migration of HUVECs in chemotaxis chambers showed that while VEGF stimulated a concentration-dependent increase in chemotaxis, PlGF caused no detectable increase in the concentration range 5-60 ng/ml.

VEGF activates p42/p44 MAP kinases in HUVEC. Given that MAP kinases have been implicated in $cPLA_2$ activation by other factors, this raised the possibility that the MAP kinase cascade might mediate VEGF-induced $PGI_2$ synthesis and $cPLA_2$ activation. The concentration-dependence for VEGF-stimulated activation of p42/p44 MAP kinases activity in confluent HUVEC was examined. Exposure of cells to VEGF for 15 min caused a detectable increase in activity at a concentration as low as 0.5 ng/ml, a half-maximal increase between 1 and 5 ng/ml, and a maximum effect at 10 ng/ml which was sustained up to 50 ng/ml. In contrast to the striking effect of VEGF, PlGF in the concentration range 1-60 ng/ml caused little, if any, detectable increase in MAP kinase activity in HUVEC. VEGF stimulation of p42/p44 MAP kinases was completely inhibited by a 30 min pretreatment with PD98059, a selective inhibitor of MAP kinase kinase (Dudley et al, PNAS USA (1995) 92:7686-7689), the dual-specificity threonine and tyrosine kinase which specifically phosphorylates and activates p42/p44 MAP kinases. The effect of the inhibitor was concentration-dependent with greater than 50% inhibition at 5 mM and a reduction of MAP kinase activity to the control, unstimulated level at 10-20 mM.

The role of the MAP kinase cascade in the VEGF-induced arachidonic acid mobilization pathway was initially investigated by examining the effect of PD98059 on $PGI_2$ synthesis. Pretreatment of HUVEC with 30 mM PD98059 for 30 min completely inhibited $PGI_2$ production induced by a subsequent 60 min incubation with either 25 ng/ml VEGF or 1 U/ml thrombin. The effect of PD98059 on VEGF-induced $PGI_2$ synthesis was concentration-dependent with a half-maximal effect at approximately 5 mM and a maximum inhibitory effect on stimulated $PGI_2$ production at 10 mM. It was also noted that PD98059 reduced $PGI_2$ production in VEGF-treated cells to below the values measured in control cells, though this effect was only apparent at concentrations of the inhibitor greater than 10 mM.

It was next tested whether PD98059 had any effect on the VEGF-induced decrease in the electrophoretic mobility of $cPLA_2$. Pretreatment with PD98059 at 25 mM completely blocked the VEGF-stimulated increase in the slow-migrating form of $cPLA_2$. Similarly to the effects of PD98059 on $PGI_2$ synthesis, the inhibitor not only reversed the VEGF-dependent decrease in $cPLA_2$ gel mobility, but also decreased the immunoreactivity of the slower-migrating form below, and increased that of the faster-migrating form above control levels.

The selectivity of the effect of PD98059 for VEGF-induced $cPLA_2$ activation and $PGI_2$ synthesis was investigated by testing whether VEGF-stimulated vWF production was also susceptible to inhibition by PD98059. In contrast to the effect of PD98059 on $cPLA_2$ activation and $PGI_2$ synthesis, pretreatment of HUVECs with the MAP kinase kinase inhibitor at 25 mM neither prevented nor significantly reduced the secretion of vWF caused by a subsequent addition of VEGF. PD98059 also had no effect either on basal or thrombin-stimulated vWF secretion.

Summary: VEGF stimulated a time- and concentration-dependent increase in $PGI_2$ synthesis which was detectable within 15 min, half-maximal at 10 ng/ml and maximal at 15 ng/ml after 60 min. In 10 independent experiments, mean maximum VEGF-stimulated $PGI_2$ synthesis was 2-fold above basal levels at 25 ng/ml after 60 min. The VEGF-related factor, placenta growth factor (PlGF), induced a much weaker 1.3-foid increase. and thrombin (1 U/ml, 60 min) induced a mean maximum increase of 4.4-fold above control levels. VEGF stimulated the release of arachidonic acid from HUVEC with a similar concentration-dependence to that obtained for $PGI_2$ synthesis but with more rapid kinetics: half-maximum arachidonic acid mobilization occurred after 10 min and was maximal after 30 min. Measurement of cytosolic phospholipase $A_2$ ($cPLA_2$) activation using mobility shift in SDS-PAGE as a marker of activation, showed that VEGF stimulated $cPLA_2$ activity in a time- and concentration-dependent manner: an increase in the slow-migrating and activated form of $cPLA_2$ occurred as early as 2 min and was detectable as low as 2.5 ng/ml, and reached a maximum after 15 min and at 5 ng/ml. Similar to other agents which induce $PGI_2$ synthesis, VEGF also caused a striking time- and concentration-dependent increase in secretion of von Willebrand factor (vWF) in HUVEC which was detectable within 30 min, half-maximal at 10 ng/ml and reached 2.5-fold above control levels after a 3 h treatment with 25 ng/ml VEGF. VEGF induced a rapid and transient activation of p42/p44 MAP kinases which was detectable as low as 1 ng/ml and reached a maximum at 5-10 ng/ml. In contrast, PlGF had little effect on MAP kinase activity. PD98059, a selective inhibitor of MAP kinase kinase, caused complete inhibition of VEGF-stimulated MAP kinase activity, $PGI_2$ synthesis and $cPLA_2$ gel retardation, but had no effect on VEGF-induced vWF secretion. These findings provide the first evidence that VEGF can stimulate $PGI_2$ synthesis via $cPLA_2$-mediated arachidonic acid release. These findings also indicate that VEGF stimulation of this biosynthetic pathway may occur, at least in part, via activation of p42/p44 MAP kinases.

The results presented here show that VEGF stimulates a striking time- and concentration-dependent increase in $PGI_2$ production in HUVEC. The effect of VEGF was weaker than that of thrombin, though the responses to the two factors varied on average by a factor of only 2.5. VEGF stimulates the rapid mobilization of arachidonic acid from human endothelial cells and, as judged by a gel retardation assay, the rapid activation of $cPLA_2$. The method used for determining the effect of VEGF on arachidonic acid mobilization is based upon the release of $^3H$-label from cells prelabelled with $^3H$-arachidonic acid. Since the studies of arachidonic acid release were performed with BSA present in the medium, it is highly likely that the major product released from HUVECs is $^3H$-arachidonic acid. The concentration-dependencies for VEGF-induced $PGI_2$ production, arachidonic acid release and $cPLA_2$ activation were similar to each other (all within the range 5-10 ng/ml). These results indicate that VEGF stimulation of arachidonic acid release and $PGI_2$ synthesis are mediated through high-affinity receptors for this factor in HUVECs.

Arachidonic acid release and the $cPLA_2$ mobility shift both occurred more rapidly than $PGI_2$ synthesis, consistent with the notion that increased production of $PGI_2$ is very likely, at least in part, to be a direct consequence of increased $cPLA_2$ activity and a subsequent increase in the availability of intracellular arachidonic acid, the substrate for the constitutive enzyme COX-1. Since VEGF is known to stimulate phospholipase C-g tyrosine phosphorylation and phosphoinositide metabolism, it is entirely plausible that other mechanisms including the sequential action of phospholipase C-g (and/or phospholipase D) and diacyl- and monacylglycerol lipases, may also contribute to VEGF-induced arachidonic acid mobilization of $PGI_2$ synthesis.

It was also investigated whether the VEGF-related factor, PlGF, a specific ligand for Flt-1, could stimulate the generation of $PGI_2$. The results suggest that PlGF can induce $PGI_2$ synthesis but more weakly than VEGF. No significant effect of PlGF was detected on either arachidonic acid release or $cPLA_2$ mobility shift. Since PlGF binds with high-affinity only to the Flt-1 VEGF receptor, these results are most consistent with the conclusion that stimulation of $PGI_2$ production by VEGF in HUVECs is mediated primarily by KDR/Flk-1 receptors, but that Flt-1 may also contribute to stimulation of this pathway. However, any Flt-1-mediated $PGI_2$ synthesis would appear to involve a mechanism other than $cPLA_2$ phosphorylation. At least two explanations could account for the relatively lower response to PlGF. Either Flt-1 induces a weaker response, and/or Flt-1 is present at lower levels than KDR/Flk-1.

The results presented herein show that VEGF induced secretion of vWF in a time- and concentration-dependent manner. The concentration-dependence for the effect of VEGF on vWF secretion agreed closely with that for $PGI_2$ synthesis and arachidonic acid mobilization. In contrast to the relatively weak effect of PlGF on $PGI_2$ synthesis, PlGF did not stimulate a detectable increase in vWF release by HUVECs.

The finding that VEGF causes a rapid shift in the electrophoretic mobility of $cPLA_2$ is consistent with increased phosphorylation, and hence activation, of the p42/p44 MAP kinases. This is supported by the finding presented here that thrombin, which is known to stimulate $cPLA_2$ phosphorylation and activation in platelets, caused a similar shift in $cPLA_2$ mobility in HUVECs. The results presented here also show that VEGF activates p42/p44 MAP kinases and that inhibition of this pathway with a selective inhibitor of MAP kinase kinase, PD98059, blocks $PGI_2$ production and the increased gel retardation of $cPLA_2$ induced by VEGF. The effect of PD98059 was at least partially selective since it had no effect on vWF secretion stimulated either by VEGF or by thrombin.

In contrast to the striking effect of VEGF, PlGF failed to significantly increase MAP kinase activity. The apparent inability of PlGF to stimulate MAP kinase activity is broadly in accord with the much weaker effect of this factor on $PGI_2$ production compared to VEGF and with the apparent inability of this factor to promote $cPLA_2$ gel retardation.

Assays of $PGI_2$ production in HUVEC indicated the presence of a significant basal level of synthesis. Interestingly the MAP kinase kinase inhibitor also abolished $PGI_2$ production in control, unstimulated cells. Consistent with the mediation of $PGI_2$ generation through activation of the MAP kinase cascade, PD98059 also reduced the level of the slow-migrating phosphorylated form of $cPLA_2$ below the control level and increased that of the fast-migrating less phosphorylated form above the control level. Assays of MAP kinase activity suggested a significant level of basal activity which was also inhibitable by PD98059. These findings suggest that MAP kinase activation may be responsible not only for VEGF- and thrombin-dependent $cPLA_2$ activation, but that basal MAP kinase activity may also be required for the maintenance of constitutive $cPLA_2$ activity and $PGI_2$ production.

It is plausible that other signalling mechanisms may contribute to VEGF stimulation of $PGI_2$ synthesis and arachidonic acid release, including elevation of intracellular $[Ca^{2+}]$.

VEGF has to date primarily been regarded as an angiogenic factor which promotes endothelial cell growth and migration. The findings presented here reveal additional activities, and may therefore have important implications both for the regulation of endothelial function and for understanding the function of VEGF, as well as for the treatment and prevention of blood vessel disorders such as stenosis, restenosis, atherosclerosis and hypertension.

We claim:

1. A device for use in the delivery of a therapeutic agent to a blood vessel in a patient, which comprises a body composed of a biodegradable material and adapted to provide a continuous seal around the vessel, the body having a wall which, with an adventitial surface of the vessel, defines a reservoir within which the agent is held and comes into contact with the adventitial surface of the vessel, wherein the reservoir is at least part-filled by a pharmaceutical formulation containing the agent to be delivered, and wherein the body material has a thickness that is smaller in an intermediate portion of the body than at spaced-apart portions of the body that seal against the vessel, the reduced thickness forming the reservoir.

2. The device according to claim 1, wherein said formulation is in the form of a fluid or gel that is injectable into the reservoir or a paste.

3. The device according to claim 2, wherein the material of the body is self-sealing.

4. The device according to claim 1, wherein said reservoir can contain up to 10 ml of fluid.

5. The device according to claim 1, wherein the body wall comprises an inner surface, wherein said inner surface comprises a sponge-like material which is capable of being impregnated with a pharmaceutical formulation containing the agent.

6. The device according to claim 1, wherein the body wall comprises an inner surface that is impregnated with a pharmaceutical formulation containing the agent.

7. The device according to claim 1, wherein said biodegradable material is gelatin, alginate or collagen.

8. The device according to claim 1, wherein said body is moulded or extruded.

9. The device according to claim 1, wherein said body comprises flexible seal portions that can accommodate expansion of the blood vessel caused by pulsatile blood flow.

10. The device according to claim 1, wherein said body comprises elongate seal portions 8 to 15 mm long.

11. The device according to claim 1, wherein said body is tubular.

12. The device according to claim 1, wherein said body has two tubular portions which are branched, to form a Y- or T-shaped body.

13. The device according to claim 1, wherein said body has three tubular portions which, at least in use, are branched, to form an X-shaped body.

14. The device according to claim 12, wherein one body portion is arcuate in cross-section transverse to its longitudinal extent so as to enable it to surround the exposed portion of a first blood vessel when that vessel is part-embedded in tissue, and longitudinally-extending edges of the first body portion are arranged to be sealed, in use, to the adventitial wall of the first blood vessel or to adjacent tissue.

15. The device according to claim 1, wherein said body has a longitudinal slit, to facilitate its fitment over the blood vessel.

16. The device according to claim 1, wherein said body includes an inner layer or helical reinforcement, to increase torsional strength.

17. The device according to claim 13, wherein one body portion is arcuate in cross-section transverse to its longitudinal extent so as to enable it to surround the exposed portion of a first blood vessel when that vessel is part-embedded in tissue, and longitudinally-extending edges of the first body portion are arranged to be sealed, in use, to the adventitial wall of the first blood vessel or to adjacent tissue.

18. The device according to claim 1, wherein said reservoir can contain at least 2 ml to 5 ml of fluid.

19. A device for use in the delivery of a therapeutic agent to a blood vessel in a patient, which comprises a body composed of a biodegradable material and adapted to provide a continuous seal around the vessel, the body having a wall which, with an adventitial surface of the vessel, defines a reservoir within which the agent is held and comes into contact with the adventitial surface of the vessel, wherein the reservoir is at least part-filled by a pharmaceutical formulation containing the agent to be delivered, and wherein the body material has a thickness that is generally constant along the length of said body material, the reservoir being formed in use by a ballooning of that portion of the body located between spaced-apart portions of the body that seal against the vessel, and wherein the body has a longitudinal slit, to facilitate its fitment over the blood vessel, wherein the facing longitudinal edges of the slit can be sealed to one another to provide the sealed reservoir.

20. The device according to claim 19, wherein the body wall comprises an inner surface, wherein said inner surface comprises a sponge-like material which is capable of being impregnated with a pharmaceutical formulation containing the agent.

21. The device according to claim 19, wherein the body wall comprises an inner surface that is impregnated with a pharmaceutical formulation containing the agent.

22. The device according to claim 19, wherein said biodegradable material is gelatin, alginate or collagen.

23. The device according to claim 19, wherein said body has two tubular portions which are branched, to form a Y- or T-shaped body.

24. The device according to claim 19, wherein said body has three tubular portions which, at least in use, are branched, to form an X-shaped body.

25. The device according to claim 23, wherein one body portion is arcuate in cross-section transverse to its longitudinal extent so as to enable it to surround the exposed portion of a first blood vessel when that vessel is part-embedded in tissue, and longitudinally-extending edges of the first body portion are arranged to be sealed, in use, to the adventitial wall of the first blood vessel or to adjacent tissue.

26. The device according to claim 19, wherein said body includes an inner layer or helical reinforcement, to increase torsional strength.

27. The device according to claim 24, wherein one body portion is arcuate in cross-section transverse to its longitudinal extent so as to enable it to surround the exposed portion of a first blood vessel when that vessel is part-embedded in tissue, and longitudinally-extending edges of the first body portion are arranged to be sealed, in use, to the adventitial wall of the first blood vessel or to adjacent tissue.

28. A device for use in the delivery of a therapeutic agent to a blood vessel in a patient, which comprises a body composed of a biodegradable material selected from the group consisting of gelatin, alginate, and collagen and adapted to provide a continuous seal around the vessel, the body having a wall which, with an adventitial surface of the vessel, defines a reservoir within which the agent is held and comes into contact with the adventitial surface of the vessel and wherein the body has a longitudinal slit, to facilitate its fitment over the blood vessel, wherein the facing longitudinal edges of the slit can be sealed to one another to provide the sealed reservoir.

29. The device according to claim 19, wherein said reservoir can contain at least 2 ml to 5 ml of fluid.

* * * * *

SEQUENCE LISTING

<160> NUMBER OF SEQ ID NOS: 10

<210> SEQ ID NO 1
<211> LENGTH: 441
<212> TYPE: DNA
<213> ORGANISM: Homo sapiens
<220> FEATURE:
<221> NAME/KEY: CDS
<222> LOCATION: 1..441

<400> SEQUENCE: 1

```
atg aac ttt ctg ctg tct tgg gtg cat tgg agc ctc gcc ttg ctg ctc        48
Met Asn Phe Leu Leu Ser Trp Val His Trp Ser Leu Ala Leu Leu Leu
 1               5                  10                  15 tac ctc cac cat gcc aag tgg tcc cag gct gca ccc atg gca gaa gga        96
Tyr Leu His His Ala Lys Trp Ser Gln Ala Ala Pro Met Ala Glu Gly
             20                  25                  30 gga ggg cag aat cat cac gaa gtg gtg aag ttc atg gat gtc tat cag       144
Gly Gly Gln Asn His His Glu Val Val Lys Phe Met Asp Val Tyr Gln
         35                  40                  45 cgc agc tac tgc cat cca atc gag acc ctg gtg gac atc ttc cag gag       192
Arg Ser Tyr Cys His Pro Ile Glu Thr Leu Val Asp Ile Phe Gln Glu
     50                  55                  60 tac cct gat gag atc gag tac atc ttc aag cca tcc tgt gtg ccg ctg       240
Tyr Pro Asp Glu Ile Glu Tyr Ile Phe Lys Pro Ser Cys Val Pro Leu
 65                  70                  75                  80 atg cga tgc ggg ggc tgc tgc aat gac gag ggc ctg gag tgt gtg ccc       288
Met Arg Cys Gly Gly Cys Cys Asn Asp Glu Gly Leu Glu Cys Val Pro
                 85                  90                  95 act gag gag tcc aac atc acc atg cag att atg cgg atc aaa cct cac       336
Thr Glu Glu Ser Asn Ile Thr Met Gln Ile Met Arg Ile Lys Pro His
            100                 105                 110 caa ggc cag cac ata gga gag atg agc ttc cta cag cac aac aaa tgt       384
Gln Gly Gln His Ile Gly Glu Met Ser Phe Leu Gln His Asn Lys Cys
        115                 120                 125 gaa tgc aga cca aag aaa gat aga gca aga caa gaa aaa tgt gac aag       432
Glu Cys Arg Pro Lys Lys Asp Arg Ala Arg Gln Glu Lys Cys Asp Lys
    130                 135                 140 ccg agg cgg                                                            441
Pro Arg Arg
145
```

<210> SEQ ID NO 2
<211> LENGTH: 147
<212> TYPE: PRT
<213> ORGANISM: Homo sapiens

<400> SEQUENCE: 2

```
Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
             20                  25                  30

Gly Gly Gln Asn His His Glu Val Val Lys Phe Met Asp Val Tyr Gln
         35                  40                  45

Arg Ser Tyr Cys His Pro Ile Glu Thr Leu Val Asp Ile Phe Gln Glu
     50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
```

```
                     85                  90                   95
Thr Glu Glu Ser Asn Ile Thr Met Gln Ile Met Arg Ile Lys Pro His
                100                 105                 110
Gln Gly Gln His Ile Gly Glu Met Ser Phe Leu Gln His Asn Lys Cys
            115                 120                 125
Glu Cys Arg Pro Lys Lys Asp Arg Ala Arg Gln Glu Lys Cys Asp Lys
        130                 135                 140
Pro Arg Arg
145

<210> SEQ ID NO 3
<211> LENGTH: 573
<212> TYPE: DNA
<213> ORGANISM: Homo sapiens
<220> FEATURE:
<221> NAME/KEY: CDS
<222> LOCATION: 1..573

<400> SEQUENCE: 3 atg aac ttt ctg ctg tct tgg gtg cat tgg agc ctc gcc ttg ctg ctc     48
Met Asn Phe Leu Leu Ser Trp Val His Trp Ser Leu Ala Leu Leu Leu
  1               5                  10                  15 tac ctc cac cat gcc aag tgg tcc cag gct gca ccc atg gca gaa gga     96
Tyr Leu His His Ala Lys Trp Ser Gln Ala Ala Pro Met Ala Glu Gly
             20                  25                  30 gga ggg cag aat cat cac gaa gtg gtg aag ttc atg gat gtc tat cag    144
Gly Gly Gln Asn His His Glu Val Val Lys Phe Met Asp Val Tyr Gln
         35                  40                  45 cgc agc tac tgc cat cca atc gag acc ctg gtg gac atc ttc cag gag    192
Arg Ser Tyr Cys His Pro Ile Glu Thr Leu Val Asp Ile Phe Gln Glu
     50                  55                  60 tac cct gat gag atc gag tac atc ttc aag cca tcc tgt gtg ccg ctg    240
Tyr Pro Asp Glu Ile Glu Tyr Ile Phe Lys Pro Ser Cys Val Pro Leu
 65                  70                  75                  80 atg cga tgc ggg ggc tgc tgc aat gac gag ggc ctg gag tgt gtg ccc    288
Met Arg Cys Gly Gly Cys Cys Asn Asp Glu Gly Leu Glu Cys Val Pro
                 85                  90                  95 act gag gag tcc aac atc acc atg cag att atg cgg atc aaa cct cac    336
Thr Glu Glu Ser Asn Ile Thr Met Gln Ile Met Arg Ile Lys Pro His
                100                 105                 110 caa ggc cag cac ata gga gag atg agc ttc cta cag cac aac aaa tgt    384
Gln Gly Gln His Ile Gly Glu Met Ser Phe Leu Gln His Asn Lys Cys
            115                 120                 125 gaa tgc aga cca aag aaa gat aga gca aga caa gaa aaa ccc tgt ggg    432
Glu Cys Arg Pro Lys Lys Asp Arg Ala Arg Gln Glu Lys Pro Cys Gly
        130                 135                 140 cct tgc tca gag cgg aga aag cat ttg ttt gta caa gat ccg cag acg    480
Pro Cys Ser Glu Arg Arg Lys His Leu Phe Val Gln Asp Pro Gln Thr
145                 150                 155                 160 tgt aaa tgt tcc tgc aaa aac aca gac tcg cgt tgc aag gcg agg cag    528
Cys Lys Cys Ser Cys Lys Asn Thr Asp Ser Arg Cys Lys Ala Arg Gln
                165                 170                 175 ctt gag tta aac gaa cgt act tgc aga tgt gac aag ccg agg cgg        573
Leu Glu Leu Asn Glu Arg Thr Cys Arg Cys Asp Lys Pro Arg Arg
            180                 185                 190

<210> SEQ ID NO 4
<211> LENGTH: 191
<212> TYPE: PRT
<213> ORGANISM: Homo sapiens
```

<400> SEQUENCE: 4

```
Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
               100                 105                 110

Gln Gly Gln His Ile Gly Glu Met Ser Phe Leu Gln His Asn Lys Cys
           115                 120                 125

Glu Cys Arg Pro Lys Lys Asp Arg Ala Arg Gln Glu Lys Pro Cys Gly
       130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
               165                 170                 175

Leu Glu Leu Asn Glu Arg Thr Cys Arg Cys Asp Lys Pro Arg Arg
           180                 185                 190
```

<210> SEQ ID NO 5
<211> LENGTH: 645
<212> TYPE: DNA
<213> ORGANISM: Homo sapiens
<220> FEATURE:
<221> NAME/KEY: CDS
<222> LOCATION: 1..645

<400> SEQUENCE: 5

```
atg aac ttt ctg ctg tct tgg gtg cat tgg agc ctc gcc ttg ctg ctc      48
Met Asn Phe Leu Leu Ser Trp Val His Trp Ser Leu Ala Leu Leu Leu
 1               5                  10                  15 tac ctc cac cat gcc aag tgg tcc cag gct gca ccc atg gca gaa gga      96
Tyr Leu His His Ala Lys Trp Ser Gln Ala Ala Pro Met Ala Glu Gly
                20                  25                  30 gga ggg cag aat cat cac gaa gtg gtg aag ttc atg gat gtc tat cag     144
Gly Gly Gln Asn His His Glu Val Val Lys Phe Met Asp Val Tyr Gln
            35                  40                  45 cgc agc tac tgc cat cca atc gag acc ctg gtg gac atc ttc cag gag     192
Arg Ser Tyr Cys His Pro Ile Glu Thr Leu Val Asp Ile Phe Gln Glu
        50                  55                  60 tac cct gat gag atc gag tac atc ttc aag cca tcc tgt gtg ccg ctg     240
Tyr Pro Asp Glu Ile Glu Tyr Ile Phe Lys Pro Ser Cys Val Pro Leu
 65                  70                  75                  80 atg cga tgc ggg ggc tgc tgc aat gac gag ggc ctg gag tgt gtg ccc     288
Met Arg Cys Gly Gly Cys Cys Asn Asp Glu Gly Leu Glu Cys Val Pro
                85                  90                  95 act gag gag tcc aac atc acc atg cag att atg cgg atc aaa cct cac     336
Thr Glu Glu Ser Asn Ile Thr Met Gln Ile Met Arg Ile Lys Pro His
               100                 105                 110 caa ggc cag cac ata gga gag atg agc ttc cta cag cac aac aaa tgt     384
Gln Gly Gln His Ile Gly Glu Met Ser Phe Leu Gln His Asn Lys Cys
```

```
                    115                 120                 125
gaa tgc aga cca aag aaa gat aga gca aga caa gaa aaa aaa tca gtt         432
Glu Cys Arg Pro Lys Lys Asp Arg Ala Arg Gln Glu Lys Lys Ser Val
    130                 135                 140 cga gga aag gga aag ggg caa aaa cga aag cgc aag aaa tcc cgg tat         480
Arg Gly Lys Gly Lys Gly Gln Lys Arg Lys Arg Lys Lys Ser Arg Tyr
145                 150                 155                 160 aag tcc tgg agc gtg ccc tgt ggg cct tgc tca gag cgg aga aag cat         528
Lys Ser Trp Ser Val Pro Cys Gly Pro Cys Ser Glu Arg Arg Lys His
                165                 170                 175 ttg ttt gta caa gat ccg cag acg tgt aaa tgt tcc tgc aaa aac aca         576
Leu Phe Val Gln Asp Pro Gln Thr Cys Lys Cys Ser Cys Lys Asn Thr
            180                 185                 190 gac tcg cgt tgc aag gcg agg cag ctt gag tta aac gaa cgt act tgc         624
Asp Ser Arg Cys Lys Ala Arg Gln Leu Glu Leu Asn Glu Arg Thr Cys
        195                 200                 205 aga tgt gac aag ccg agg cgg                                             645
Arg Cys Asp Lys Pro Arg Arg
    210                 215

<210> SEQ ID NO 6
<211> LENGTH: 215
<212> TYPE: PRT
<213> ORGANISM: Homo sapiens

<400> SEQUENCE: 6

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
        195                 200                 205

Arg Cys Asp Lys Pro Arg Arg
    210                 215

<210> SEQ ID NO 7
<211> LENGTH: 696
```

<212> TYPE: DNA
<213> ORGANISM: Homo sapiens
<220> FEATURE:
<221> NAME/KEY: CDS
<222> LOCATION: 1..696

<400> SEQUENCE: 7

```
atg aac ttt ctg ctg tct tgg gtg cat tgg agc ctg gcc ttg ctg ctc      48
Met Asn Phe Leu Leu Ser Trp Val His Trp Ser Leu Ala Leu Leu Leu
 1               5                  10                  15 tac ctc cac cat gcc aag tgg tcc cag gct gca ccc atg gca gaa gga      96
Tyr Leu His His Ala Lys Trp Ser Gln Ala Ala Pro Met Ala Glu Gly
                 20                  25                  30 gga ggg cag aat cat cac gaa gtg gtg aag ttc atg gat gtc tat cag     144
Gly Gly Gln Asn His His Glu Val Val Lys Phe Met Asp Val Tyr Gln
         35                  40                  45 cgc agc tac tgc cat cca atc gag acc ctg gtg gac atc ttc cag gag     192
Arg Ser Tyr Cys His Pro Ile Glu Thr Leu Val Asp Ile Phe Gln Glu
     50                  55                  60 tac cct gat gag atc gag tac atc ttc aag cca tcc tgt gtg ccg ctg     240
Tyr Pro Asp Glu Ile Glu Tyr Ile Phe Lys Pro Ser Cys Val Pro Leu
 65                  70                  75                  80 atg cga tgc ggg ggc tgc tgc aat gac gag ggc ctg gag tgt gtg ccc     288
Met Arg Cys Gly Gly Cys Cys Asn Asp Glu Gly Leu Glu Cys Val Pro
                 85                  90                  95 act gag gag tcc aac atc acc atg cag att atg cgg atc aaa cct cac     336
Thr Glu Glu Ser Asn Ile Thr Met Gln Ile Met Arg Ile Lys Pro His
                100                 105                 110 caa ggc cag cac ata gga gag atg agc ttc cta cag cac aac aaa tgt     384
Gln Gly Gln His Ile Gly Glu Met Ser Phe Leu Gln His Asn Lys Cys
            115                 120                 125 gaa tgc aga cca aag aaa gat aga gca aga caa gaa aaa aaa tca gtt     432
Glu Cys Arg Pro Lys Lys Asp Arg Ala Arg Gln Glu Lys Lys Ser Val
        130                 135                 140 cga gga aag gga aag ggg caa aaa cga aag cgc aag aaa tcc cgg tat     480
Arg Gly Lys Gly Lys Gly Gln Lys Arg Lys Arg Lys Lys Ser Arg Tyr
145                 150                 155                 160 aag tcc tgg agc gtg tac gtt ggt gcc cgc tgc tgt cta atg ccc tgg     528
Lys Ser Trp Ser Val Tyr Val Gly Ala Arg Cys Cys Leu Met Pro Trp
                165                 170                 175 agc ctc cct ggc ccc cat ccc tgt ggg cct tgc tca gag cgg aga aag     576
Ser Leu Pro Gly Pro His Pro Cys Gly Pro Cys Ser Glu Arg Arg Lys
            180                 185                 190 cat ttg ttt gta caa gat ccg cag acg tgt aaa tgt tcc tgc aaa aac     624
His Leu Phe Val Gln Asp Pro Gln Thr Cys Lys Cys Ser Cys Lys Asn
        195                 200                 205 aca gac tcg cgt tgc aag gcg agg cag ctt gag tta aac gaa cgt act     672
Thr Asp Ser Arg Cys Lys Ala Arg Gln Leu Glu Leu Asn Glu Arg Thr
210                 215                 220 tgc aga tgt gac aag ccg agg cgg                                     696
Cys Arg Cys Asp Lys Pro Arg Arg
225                 230
```

<210> SEQ ID NO 8
<211> LENGTH: 232
<212> TYPE: PRT
<213> ORGANISM: Homo sapiens

<400> SEQUENCE: 8

```
Met Asn Phe Leu Leu Ser Trp Val His Trp Ser Leu Ala Leu Leu Leu
 1               5                  10                  15
```

-continued

```
Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
 50                      55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
            195                 200                 205

Thr Asp Ser Arg Cys Lys Ala Arg Gln Leu Glu Leu Asn Glu Arg Thr
210                 215                 220

Cys Arg Cys Asp Lys Pro Arg Arg
225                 230
```

```
<210> SEQ ID NO 9
<211> LENGTH: 20
<212> TYPE: DNA
<213> ORGANISM: Homo sapiens

<400> SEQUENCE: 9
tcgatccatg aactttctgc                                               20

<210> SEQ ID NO 10
<211> LENGTH: 20
<212> TYPE: DNA
<213> ORGANISM: Homo sapiens

<400> SEQUENCE: 10
tccgtttaac tcaagctgcc                                               20
```